US008097776B2

(12) United States Patent
Primard-Brisset et al.

(10) Patent No.: US 8,097,776 B2
(45) Date of Patent: *Jan. 17, 2012

(54) **METHOD OF PRODUCING DOUBLE LOW RESTORER LINES OF *BRASSICA NAPUS* HAVING A GOOD AGRONOMIC VALUE**

(75) Inventors: Catherine Primard-Brisset, Saint Remy les Chevreuse (FR); Régine Delourme, L'Hermitage (FR); Jean-Pierre Poupard, Versailles (FR); Nicolas Pierre Poupard, legal representative, Chilly-Mazarin (FR); Marion Hélène Poupard, legal representative, Longjumeau (FR); Raymonde Horvais, Montreuil-sur-Ille (FR); Françoise Budar, Les Molières (FR); Georges Pelletier, Bures sur Yvette (FR); Michel Renard, Le Rheu (FR)

(73) Assignee: Institut National de la Recherche Agronomique (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/815,921

(22) Filed: Jun. 15, 2010

(65) Prior Publication Data

US 2010/0299779 A1 Nov. 25, 2010

Related U.S. Application Data

(63) Continuation of application No. 10/563,277, filed as application No. PCT/IB2004/002491 on Jul. 5, 2004, now Pat. No. 7,812,217.

(30) Foreign Application Priority Data

Jul. 4, 2003 (EP) .................................... 03291677
Dec. 8, 2003 (EP) .................................... 03293057

(51) Int. Cl.
*A01H 1/02* (2006.01)
*A01H 5/00* (2006.01)
*A01H 5/10* (2006.01)
*C12N 15/10* (2006.01)
*C12N 15/29* (2006.01)

(52) U.S. Cl. ........ 800/306; 800/267; 800/274; 800/276; 800/303; 435/6.11; 435/6.12

(58) Field of Classification Search ........................ None
See application file for complete search history.

(56) References Cited

FOREIGN PATENT DOCUMENTS

WO 98/27806 A1 7/1998

OTHER PUBLICATIONS

Desloire et al., "Identification of the fertility restoration locus, Rfo, in radish, as a member of the pentatricopeptide-repeat protein family", EMBO reports vol. 4, No. 6, pp. 588-594, Jun. 6, 2003.
Delourme et al., Characterisation of the radish introgression carrying the Rfo, restorer gene for the Ogu-INRA cytoplasmic male sterility in rapeseed (*Brassica napus* I.), Theoretical and Applied Genetics, vol. 97, No. 1-2, pp. 129-134, Jul. 1998.
Delourme et al., Linkage between an isozyme marker and a restorer gene in radish cytoplasmic male sterility of rapeseed (*Brassica napus* L.), Theoretical and Applied Genetics, vol. 85, pp. 222-228, Springer, Berlin, DE, (1992).
Delourme et al., Identification of RAPD markers linked to a fertility restorer gene for the Ogura radish cytoplasmic male sterility of rapeseed (*Brassica napus* L.), Theoretical and Applied Genetics, vol. 88, No. 6/7, pp. 741-748, 1994, Springer, Berlin, DE.
Bellaoui et al., "The resotorer Rfo gene acts post-translationally on the stability of the ORF138 CMS-associated protein in reproductive tissue of rapeseed cybrids", vol. 40, No. 5, pp. 893-902, Jul. 1999, Plant Molecular Biology, NIJHOFF publishers, Dordrecht, NL.
Giancola et al., "Characterization of a radish introgression carrying the Ogura fertility restorer gene Rfo in rapeseed, using the *Arabidopsis* genome sequence and radish genetic mapping", TAG. Theoretical and Applied Genetics. vol. 107, No. 8, pp. 1442-1451, Aug. 27, 2003 Germany.
Fourmann et al., "From *Arabidopsis thaliana* to *Brassica napus*: development of amplified consensus genetic markers (ACGM) for construction of a gene map", Theor . Appl. Genet, vol. 105, pp. 1196-1206, 2002.
Delourme et al., "Double Low Restored F1 Hybrids Can Be Produced With the Ogu-INRA CMS in Rapeseed", 10th Rapeseed Congress, Canaberra 1999, pp. 26-29.
Pellan-Delourme et al. Genome 30: 234-238 (1988).
Primard-Brisset et al. Theoretical and Applied Genetics 11 : 736-746 (2005).
Bartkowiak-Broda et al. 1999. Proceedings of the 10th International Rapeseed Congress, Camberra, Australia, pp. 1-5.
Delourme et al. 1999. Proceedings of the 10th International Rapeseed Congress, Camberra, Australia, pp. 6-9.
Delourme R et al: "Breeding Double Low Restorer Lines in Radish Cytoplasmic Male Sterility of Rapeseed (*Brassica Napus* L)" Proceedings 9th International Rapeseed Congress, Cambridge. UK, Jul. 4, 1995-Jul. 7, 1995 pp. 6-08, XP002575753.
European Search Report, EP 09175998, dated Apr. 22, 2010.

*Primary Examiner* — David T Fox
(74) *Attorney, Agent, or Firm* — Lerner, David, Littenberg, Krumholz & Mentlik, LLP

(57) ABSTRACT

The invention relates to a method of producing a double low restorer line of *Brassica napus* for Ogura cytoplasmic male sterility (cms) presenting a radish introgression carrying the Rfo restorer gene deleted of the radish Pgi-2 allele and recombined with the Pgi-2 gene from *Brassica oleracea*, and having a good agronomic value characterized by female fertility, a good transmission rate of Rfo and a high vegetative vigour. The invention relates also to a method of forming *Brassica napus* hybrid seeds and progeny thereof and to the use of markers for selection.

10 Claims, 25 Drawing Sheets

Fig. 1: Seed set on 'R211' and 'R2000'

Fig 3

| Genotype | Selfings | Test Crosses |
|----------|----------|--------------|
| Drakkar | 29.3 | |
| Pactol | 23.1 | |
| R211 | 11.2 | 25.5 |
| R2000 | 26.5 (24.0 – 31.1) | 27.0 (24.0 – 28.7) |

Figure 12

| | | | | | | | | | | | | |
|---|---|---|---|---|---|---|---|---|---|---|---|---|
| type B. ole | 250 | | | | | | | | | | + | |
| type B.rap | 250 | | | | + | | + | | + | | | | |
| PGI/UNT | 980 | + | + | + | + | + | - | + | + | + | + | |
| type B. ole | 980 | | + | + | + | + | - | + | + | + | - | + |
| type B.rap | 980 | | + | - | + | + | - | + | + | + | | - |
| PGI int | | | | | | | | | | | | | |
| radis | 950 | 1000 | + | + | + | - | - | + | - | - | - | - | - |
| Brassica | 870 | + | - | + | + | + | - | + | + | + | + | - |
| type B. ole | 870 | | | - | + | + | - | + | + | + | | + |
| type B.rap | 870 | | + | + | + | + | - | + | + | + | | - |
| BolJon | | | | | | | | | | | | | |
| B. ole | 950 | | + | - | + | + | - | + | + | + | + | - |
| B.rap | 870 | | | + | + | + | + | + | + | + | + | - |
| Ath | 800 | | | | | | | - | + | | + | - |
| radis | 630 | | | | | | | | | | + | |
| radis | 590 | | + | | | | | | | | - | - |
| CP418L | | | | | | | | | | | | | |
| B. ole | 670 | + | + | + | + | + | - | + | + | + | - | - |
| (approximative size band) | | | | | | | | | | | | | |
| *Brassica band is characterised by Its DNA sequence* | | | | | | | | | | | | | |

Figure 13 (a)

```
                              51                                   81 PGIo1 U --->  100
consePGIinTUNTDrakka    ..........  ..........  ..........  ..........  ..........
     consensWesrPGI     ..........  ..........  ..........  ..........  ..........
   consePGIintUNTR113   ..........  ..........  ..........  ..........  ..........
  consePGIintUNTBrapaA  ..........  ..........  ..........  ..........  ..........
  ConsePGIintUNTRRH1    ..........  ..........  ..........  ..........  ..........
    PGIBo-EM:AF258277   TTGCTTAGCG  TCCAAATTTC  ATGATTGTAT  TCATTTGATT  GTTGTG....
    PGIBra-EM:AF258278  TTGCTTAGCG  TCCAAATTTC  ATGATTGTAT  TCATTTGATT  GTTGTGTGAC
   consePGIintUNTBolera ..........  ..........  ..........  ..........  ..........
   consePGIintUNTR2000  ..........  ..........  ....TTG...  TCATT.GA..  .TTGT.TGCG
           Consensus                                                       1

101    --->                                     150
consePGIinTUNTDrakka    ..........  ......GTCG  TTTGTTGGTG  AGT.GAACAG  CAGTCATTTA
     consensWesrPGI     ..........  .GCCTGTTTG  TGTTATGATG  AAT.GAACAG  CAGTCATTTA
   consePGIintUNTR113   ..........  .GCCCGGTTG  .........G  TAT.GAAACG  CAG.CATTTA
  consePGIintUNTBrapaA  ..........  ..........  ..........  .........G  CAGTCATTTA
  ConsePGIintUNTRRH1    ..........  ..........  ..........  ........CG  TGTTGAGAAG  CAG.CATTTA
    PGIBo-EM:AF258277   ......CCTG  TCGCCTTGTT  TGTTA.GATG  AAT.GAACAG  CAGTCATTTA
    PGIBra-EM:AF258278  TATCGCCTC.  TCGCCTTGTT  TGTTATGATG  AAT.GAACAG  CAGTCATTTA
   consePGIintUNTBolera ..........  ..........  ..........  ..........  ..........
   consePGIintUNTR2000  ......CCTG  TCGCCTTGTT  TGTTATGATG  AAT.GAACA.  CAGTCATTTA
           Consensus    ..........  .......t.g  ..........  ...t.gaa.ag cagtcattta 151         * MseI restriction site         200
consePGIinTUNTDrakka    ACATG.TGGT  TAACTTAACA  GGGCTCCGGC  TGTTGCAAAA  CACATGGTTG
     consensWesrPGI     ACATG.TGGT  TAACTTAACA  GGGCTCCGGC  TGTTGCAAAA  CACATGGTTG
   consePGIintUNTR113   ACATG.TGGT  .AACTGAACA  GGGCTCCGGC  TGTTGCCC..  CTAAGGGTTG
  consePGIintUNTBrapaA  ACATGGTGGT  TAACTGAACA  GGGCTCCGGC  TGTTGCAAAA  CACATGGTTG
  ConsePGIintUNTRRH1    ACATG..GGT  ..ACTGAACA  GGGC.CCGGC  TGTTGCAA..  .ACAG...TG
    PGIBo-EM:AF258277   ACATG.TGGT  TAACTTAACA  GGGCTCAGGC  TGTTGCAAAA  CACATGGTTG
    PGIBra-EM:AF258278  ACATG.TGGT  TAACTTAACA  GGGCTCCGGC  TGTTGCAAAA  CATATGGTTG
   consePGIintUNTBolera ..........  ..........  .........C  TGTTGCAAAA  CACATGGTTG
   consePGIintUNTR2000  ACATG.TGGT  TAACTTAACA  GGGCTCCGGC  TGTTGCAAAA  CACATGGTTG
           Consensus    acatg.tggt  taact.aaca  gggctccggc  tgttgcaaaa  cacatggttg
                                        2

201   PGI int U --->                            250
consePGIinTUNTDrakka    CTGT  CAGCAC TAATCTTGC GGTATG  AATT  TGTGATTAAA  TTTGTTTGTT
     consensWesrPGI     CTGT  CAGCAC TAATCTTGC GGTATG  AATT  TGTGATTAAA  TTTGTTTGTT
   consePGIintUNTR113   CTGT  CAGCAC TAATCTTGC GGTATG  AATT  TGTGATTAAA  TTTGTTTGTT
  consePGIintUNTBrapaA  CTGT  CAGCAC TAATCTTGC GGTATG  AATT  TGTGATTAAA  TTTGTTTGTT
  ConsePGIintUNTRRH1    CTGT  CAGCAC TAATCTTGC GGTATG  AATT  TGTGATTAAA  TTTGTTTGTT
    PGIBo-EM:AF258277   CTGT  CAGCAC TAATCTTGC GGTATG  AATT  TGTGATTAAA  TTTGTTTGTT
    PGIBra-EM:AF258278  CTGT  CAGCAC TAATCTTGC GGTATG  AATT  TGTGATTAAA  TTTGTTTGTT
   consePGIintUNTBolera CTGT  CAGCAC TAATCTTGC GGTATG  AATT  TGTGATTAAA  TTTGTTTGTT
   consePGIintUNTR2000  CTGT  CAGCAC TAATCTTGC GGTATG  AATT  TGTGATTAAA  TTTGTTTGTT
           Consensus    ctgtcagcac  taatcttgc ggtatg aatt  tgtgattaaa  tttgtttgt 251                                             300
consePGIinTUNTDrakka    TGTGACTCTT  T.CTTCATTG  TTCGTTTTCG  TACAATAAAC  CGAATGTATA
     consensWesrPGI     TGTGACTCTT  T.CTTCATTG  TTCGTTTTCG  TACAATAAAC  CGAATGTATA
   consePGIintUNTR113   TGCGACTCTT  T.CTTCATTG  TTCGTTTTCG  TACAATAAAC  ...AATGTATA
  consePGIintUNTBrapaA  TGCGACTCTT  T.CTTCATTG  TTCGTTTTCG  TACAATAAAC  ...AATGTATA
  ConsePGIintUNTRRH1    TGCGACTCTT  T.CTTCATTG  TTCGTTTTCG  TACAATAAAC  ...AATGTATA
    PGIBo-EM:AF258277   TGTGACTCTT  T.CTTCATTG  TTCGTTTTCG  TACAATAAAC  CGAATGTATA
    PGIBra-EM:AF258278  TGTGACTCTT  TTCTTCATTG  TTCGTTTTCG  TACAATAAAC  CGAATGTATA
   consePGIintUNTBolera TG.GACTCTT  T.CTTCATTG  TTCGTTTTCG  TACAATAAAC  CGAATGTATA
   consePGIintUNTR2000  TGTGACTCTT  T.CTTCATTG  TTCGTTTTCG  TACAATAAAC  CGAATGTATA
           Consensus    tg.gactctt  t.cttcattg  ttcgttttcg  tacaataaac  cgaatgtata
```

Figure 13 (b)

```
                        301                        <---    PGIo1 antL 341          350
consePGIinTUNTDrakka    ATCTTTTTAC AAACTGAA         TT TTCTACCGGG TCTGATGTAC A     ATGCTAGTC
     consensWesrPGI     ATCTTTTTAC AAACTGAA         TT TTCTACCGGG TCTGATGTAC A     ATGCTAGTC
   consePGIintUNTR113   ATCTTTTTAC AAACTGAA         TT TTCTACCGGG TCTGATGTAC A     ATGCTAGTC
  consePGIintUNTBrapaA  ATCTTTTTAC AAACTGAA         TT TTCTACCGGG TCTGATGTAC A     ATGCTAGTC
   ConsePGIintUNTRRH1   ATCTTTTTAC AAACTGAA         TT TTCTACCGGG TCTGATGTAC A     ATGCTAGTC
     PGIBo-EM:AF258277  ATCTTTTTAC AAACTGAA         TT TTCTACCGGG TCTGATGTAC A     ATGCTAGTC
     PGIBra-EM:AF258278 ACCTTTTTAC AAACTGAA         AT GTCTACCGGG TCTGATGTAC A     ATGCTAGTC
  consePGIintUNTBolera  ATCTTTTTAC AAACTGAA         TT TTCTACCGGG TCTGATGTAC A     ATGCTAGTC
  consePGIintUNTR2000   ATCTTTT.AC AAACTGAA         TT TTCTACCGGG TCTGATGTAC A     ATGCTAGTC
           Consensus    atcttttac  aaactgaa         tt ttctaccggg tctgatgtac a     atgctAGTC
```

Figure 14 (a)

```
       201  PGI int U --->                                           250
consePGIinTUNTDrakka  CTGT  CAGCAC TAATCTTGC GGTATG  AATT TGTGATTAAA TTTGTTTGTT
     consensWesrPGI  CTGT  CAGCAC TAATCTTGC GGTATG  AATT TGTGATTAAA TTTGTTTGTT
   consePGIintUNTR113  CTGT  CAGCAC TAATCTTGC GGTATG  AATT TGTGATTAAA TTTGTTTGTT
  consePGIintUNTBrapaA  CTGT  CAGCAC TAATCTTGC GGTATG  AATT TGTGATTAAA TTTGTTTGTT
    ConsePGIintUNTRRH1  CTGT  CAGCAC TAATCTTGC GGTATG  AATT TGTGATTAAA TTTGTTTGTT
       PGIBo-EM:AF258277  CTGT  CAGCAC TAATCTTGC GGTATG  AATT TGTGATTAAA TTTGTTTGTT
       PGIBra-EM:AF258278  CTGT  CAGCAC TAATCTTGC GGTATG  AATT TGTGATTAAA TTTGTTTGTT
    consePGIintUNTBolera  CTGT  CAGCAC TAATCTTGC GGTATG  AATT TGTGATTAAA TTTGTTTGTT
    consePGIintUNTR2000  CTGT  CAGCAC TAATCTTGC GGTATG  AATT TGTGATTAAA TTTGTTTGTT
            Consensus  ctgtcagcac  taatcttgc ggtatg  aatt tgtgattaaa tttgtttgt 251                                                         300
consePGIinTUNTDrakka  TGTGACTCTT T.CTTCATTG TTCGTTTTCG TACAATAAAC  CGAATGTATA
     consensWesrPGI  TGTGACTCTT T.CTTCATTG TTCGTTTTCG TACAATAAAC  CGAATGTATA
   consePGIintUNTR113  TGCGACTCTT T.CTTCATTG TTCGTTTTCG TACAATAAAC  ..AATGTATA
  consePGIintUNTBrapaA  TGCGACTCTT T.CTTCATTG TTCGTTTTCG TACAATAAAC  ..AATGTATA
    ConsePGIintUNTRRH1  TGCGACTCTT T.CTTCATTG TTCGTTTTCG TACAATAAAC  ..AATGTATA
       PGIBo-EM:AF258277  TGTGACTCTT T.CTTCATTG TTCGTTTTCG TACAATAAAC  CGAATGTATA
       PGIBra-EM:AF258278  TGTGACTCTT TTCTTCATTG TTCGTTTTCG TACAATAAAC  CGAATGTATA
    consePGIintUNTBolera  TG.GACTCTT T.CTTCATTG TTCGTTTTCG TACAATAAAC  CGAATGTATA
    consePGIintUNTR2000  TGTGACTCTT T.CTTCATTG TTCGTTTTCG TACAATAAAC  CGAATGTATA
            Consensus  tg.gactctt t.cttcattg ttcgttttcg tacaataaac  cgaatgtata
                                     ε                               ε3

301                     <---  PGIol antL 341       350
consePGIinTUNTDrakka  ATCTTTTTAC AAAACTGAA TT TTCTACCGGG TCTGATGTAC A ATGCTAGTC
     consensWesrPGI  ATCTTTTTAC AAAACTGAA TT TTCTACCGGG TCTGATGTAC A ATGCTAGTC
   consePGIintUNTR113  ATCTTTTTAC AAAACTGAA TT TTCTACCGGG TCTGATGTAC A ATGCTAGTC
  consePGIintUNTBrapaA  ATCTTTTTAC AAAACTGAA TT TTCTACCGGG TCTGATGTAC A ATGCTAGTC
    ConsePGIintUNTRRH1  ATCTTTTTAC AAAACTGAA TT TTCTACCGGG TCTGATGTAC A ATGCTAGTC
       PGIBo-EM:AF258277  ATCTTTTTAC AAAACTGAA TT TTCTACCGGG TCTGATGTAC A ATGCTAGTC
       PGIBra-EM:AF258278  ACCTTTTTAC AAAACTGAA AT GTCTACCGGG TCTGATGTAC A ATGCTAGTC
    consePGIintUNTBolera  ATCTTTTTAC AAAACTGAA TT TTCTACCGGG TCTGATGTAC A ATGCTAGTC
    consePGIintUNTR2000  ATCTTTT.AC AAAACTGAA TT TTCTACCGGG TCTGATGTAC A ATGCTAGTC
            Consensus  atcttttac aaactgaa   tt ttctaccggg tctgatgtac a atgctAGTC
                        ε
       351                                                         400
consePGIinTUNTDrakka  TCCATGTTCT TGGGGATCAT GATTTATTTT CTACATGTAT TCAGACAGTA
     consensWesrPGI  TCCATGTTCT TGGGGATCAT GATTTATTTT CT.CATGTAT TCAGACAGTA
   consePGIintUNTR113  TCCATGTTCT TGGGGATCAT GATTTATTTT CTACATGTGT TCAGCCAGTA
  consePGIintUNTBrapaA  TCCATGTTCT TGGGGATCAT GATTTATTTT CTACATGTGT TCAGCCAGTA
    ConsePGIintUNTRRH1  TCCATGTTCT TGGGGATCAT GATTTATTTT CTACATGTGT TCAGCCAGTA
       PGIBo-EM:AF258277  TCCATGTTCT TGGGGATCAT GATTTATTTT CTACATGTAT TCAGACAGTA
       PGIBra-EM:AF258278  TCCATGTTCT TGGGGATCAT GATTTATTTT CTACATGTAT TCAGACAGTA
    consePGIintUNTBolera  TCCATGTTCT TGGGGATCAT GATTTATTTT CTACATGTAT TCAGACAGTA
    consePGIintUNTR2000  TCCATGTTCT TGGGGATCAT GATTTATTTT CTACATGTAT TCAGACAGTA
            Consensus  TCCATGTTCT TGGGGATCAT GATTTATTTT CTaCATGTaT TCAGaCAGTA
                                                          ε5          ε6
       401                                                         450
consePGIinTUNTDrakka  CAGAAGAAAG TGTTCAAAAC TCTGGATGTT TTAATTTACA GTTAGTGGAG
     consensWesrPGI  CAGAAGAAAG TGTTCAAAAC TCTGGATGTT TTAATTTACA GTTAGTGGAG
   consePGIintUNTR113  CAGAAGAAAG TGTTTAAAAC TCTGGATGTT TTAATTTACA GTTAGTGGAG
  consePGIintUNTBrapaA  CAGAAGAAAG TGTTTAAAAC TCTGGATGTT TTAATTTACA GTTAGTGGAG
    ConsePGIintUNTRRH1  CAGAAGAAAG TGTTTAAAAC TCTGGATGTT TTAATTTACA GTTAGTGGAG
       PGIBo-EM:AF258277  CAGAAGAAAG TATTTAAAAC TCTGGATGTT TTAATTTACA GTTAGTGGAG
       PGIBra-EM:AF258278  CAGAAGAAAA TGTTTAAAAC TCTGGATGTT TTGATTTACA GTTAGTGGAG
    consePGIintUNTBolera  CAGAAGAAAG TGTTCAAAAC TCTGGATGTT TTAATTTACA GTTAGTGGAG
    consePGIintUNTR2000  CAGAAGAAAG TGTTCAAAAC TCTGGATGTT TTAATTTACA GTTAGTGGAG
            Consensus  CAGAAGAAAg TgTTcAAAAC TCTGGATGTT TTaATTTACA GTTAGTGGAG
                          ε7                                ε
```

Figure 14 (b)

```
                         451        end of Data Base PGI sequences       500
consePGIinTUNTDrakka     AAGTTCGGCA TTGATCCGAA CAATGCATTT GCATTTTGGG ACTGGGTTGG
       consensWesrPGI    AAGTTCGGCA TTGATCCGAA CAATGCATTT GCATTTTGGG ACTGGGTTGG
    consePGIintUNTR113   AAGTTCGGCA TTGATCCGAA CAATGCATTT GCATTTTGGG ACTGGGTTGG
    consePGIintUNTBrapaA AAGTTCGGCA TTGATCCGAA CAATGCATTT GCATTTTGGG ACTGGGTTGG
    ConsePGIintUNTRRH1   AAGTTCGGCA TTGATCCGAA CAATGCATTT GCATTTTGGG ACTGGGTTGG
      PGIBo-EM:AF258277  AAGTTCGGCA TTGATCC... .......... .......... ..........
      PGIBra-EM:AF258278 AAGTTCGGCA TTGATCCGAA CAA....... .......... ..........
    consePGIintUNTBolera AAGTTCGGCA TTGATCCGAA CAATGCATTT GCATTTTGGG ACTGGGTTGG
    consePGIintUNTR2000  AAGTTCGGCA TTGATCCGAA CAATGCATTT GCATTTTGGG ACTGGGTTGG
             Consensus   AAGTTCGGCA TTGATCCgaa caatgcattt gcattttggg actgggttgg 501                                             550
consePGIinTUNTDrakka     TGGAAGGTAC AGTGGTAAGT GCTTGTTTAT TTGGTTGTAT AAATTTCTCG
       consensWesrPGI    TGGAAGGTAC AGTGGTAAGT GCTTGTTTAT TTGGTTGTAT AAATTTCTCG
    consePGIintUNTR113   TGGAAGGTAC AGTGGTAAGT GCTTGTTTAT TTGGTTGTAT TAATTTCTCA
    consePGIintUNTBrapaA TGGAAGGTAC AGTGGTAAGT GCTTGTTTAT TTGGTTGTAT TAATTTCTCA
    ConsePGIintUNTRRH1   TGGAAGGTAC AGTGGTAAGT GCTTGTTTAT TTGGTTGTAT TAATTTCTCA
      PGIBo-EM:AF258277  .......... .......... .......... .......... ..........
      PGIBra-EM:AF258278 .......... .......... .......... .......... ..........
    consePGIintUNTBolera TGGAAGGTAC AGTGGTAAGT GCTTGTTTAT TTGGTTGTAT AAATTTCTCG
    consePGIintUNTR2000  TGGAAGGTAC AGTGGTAAGT GCTTGTTTAT TTGGTTGTAT AAATTTCTCG
             Consensus   tggaaggtac agtggtaagt gcttgtttat ttggttgtat .aatttctc.
                                                                    8          9

551                                             600
consePGIinTUNTDrakka     TCCATTTCCG CTTGCTTAGT GTATAACTGA AATTCTTTTG CAGTTTGCAG
       consensWesrPGI    TCCATTTCCG CTTGCTTAGT GTATAACTGA AATTCTTTTG CAGTTTGCAG
    consePGIintUNTR113   TCCATATCCG CTTGCTTAGT TTATAACTGA AATTCTTTTG CAGTTTGCAG
    consePGIintUNTBrapaA TCCATATCCG CTTGCTTAGT TTATAACTGA AATTCTTTTG CAGTTTGCAG
    ConsePGIintUNTRRH1   TCCATATCCG CTTGCTTAGT TTATAACTGA AATTCTTTTG CAGTTTGCAG
      PGIBo-EM:AF258277  .......... .......... .......... .......... ..........
      PGIBra-EM:AF258278 .......... .......... .......... .......... ..........
    consePGIintUNTBolera TCCATTTCCG CTTGCTTAGT GTATAACTGA AATTCTTTTG CAGTTTGCAG
    consePGIintUNTR2000  TCCATTTCCG CTTGCTTAGT GTATAACTGA AATTCTTTTG CAGTTTGCAG
             Consensus   tccat.tccg cttgcttagt .tataactga aattcttttg cagtttgcag
                              10                11

601                                             650
consePGIinTUNTDrakka     TGCTGTTGGA GTCTTACCAT TGTCTCTACA GTATGGCTTC TCTGTGGTTG
       consensWesrPGI    TGCTGTTGGA GTCTTACCAT TGTCTCTACA GTATGGCTTC TCTGTGGTTG
    consePGIintUNTR113   TGCTGTTGGA GTCTTACCAT TGTCTCTACA GTATGGCTTC TCCGTGGTTG
    consePGIintUNTBrapaA TGCTGTTGGA GTCTTACCAT TGTCTCTACA GTATGGCTTC TCCGTGGTTG
    ConsePGIintUNTRRH1   TGCTGTTGGA GTCTTACCAT TGTCTCTACA GTATGGCTTC TCCGTGGTTG
      PGIBo-EM:AF258277  .......... .......... .......... .......... ..........
      PGIBra-EM:AF258278 .......... .......... .......... .......... ..........
    consePGIintUNTBolera TGCTGTTGGA GTCTTACCAT TGTCTCTACA GTATGGCTTC TCTGTGGTTG
    consePGIintUNTR2000  TGCTGTTGGA GTCTTACCAT TGTCTCTACA GTATGGCTTC TCTGTGGTTG
             Consensus   tgctgttgga gtcttaccat tgtctctaca gtatggcttc tc.gtggttg
                                                                          12

651                                             700
consePGIinTUNTDrakka     AGAAGTACGG TACCTTCTAC TTTATCAGCC ATCTCATAAA ATGTCTTAGG
       consensWesrPGI    AGAAGTACGG TACCTTCTAC TTTATCAGCC ATCTCATAAA ATGTCTTAGG
    consePGIintUNTR113   AGAAGTACGG TACCTTCTAC TTTATTAGCC ATCTCATAAA ATGTCTTGGG
    consePGIintUNTBrapaA AGAAGTACGG TACCTTCTAC TTTATTAGCC ATCTCATAAA ATGTCTTGGG
    ConsePGIintUNTRRH1   AGAAGTACGG TACCTTCTAC TTTATTAGCC ATCTCATAAA ATGTCTTGGG
      PGIBo-EM:AF258277  .......... .......... .......... .......... ..........
      PGIBra-EM:AF258278 .......... .......... .......... .......... ..........
    consePGIintUNTBolera AGAAGTACGG TACCTTCTAC TTTATCAGCC ATCTCATAAA A.GTCTTAGG
    consePGIintUNTR2000  AGAAGTACGG TACCTTCTAC TTTATCAGCC ATCTCATAAA ATGTCTTAGG
             Consensus   agaagtacgg taccttctac tttat.agcc atctcataaa atgtctt.gg
                                                             13              14
```

Figure 14 (c)

```
                          701                                                              750
consePGIinTUNTDrakka      CATATTCTTT CTATTTTATT TTCCTCTTAA TGATTTCTTC TTTTTTTTAT
consensWesrPGI            CATATTCTTT CTATTTTATT TTCCTCTTAA TGATTTCTTC TTTTTTTTAT
consePGIintUNTR113        CATATTCTTT CTATTTTATT TTCCTCTGAA TGATTTCTTC TCTTTTAT..
consePGIintUNTBrapaA      CATATTCTTT CTATTTTATT TTCCTCTGAA TGATTTCTTC TCTTTTAT..
ConsePGIintUNTRRH1        CATATTCTTT CTATTTTATT TTCCTCTGAA TGATTTCTTC TCTTTTAT..
PGIBo-EM:AF258277         .......... .......... .......... .......... ..........
PGIBra-EM:AF258278        .......... .......... .......... .......... ..........
consePGIintUNTBolera      CATATTCTTT CTATTTTATT TTCCTCTTAA TGATTTCTTC TTTTTTTA..
consePGIintUNTR2000       CATATTCTTT CTATTTTATT TCCCTCTTAA TGATTTCTTC TTTTTTTTAT
Consensus                 catattcttt ctattttatt ttcctct.aa tgatttcttc t.tttt.t..
                                                        15                   16      17
                          751                                                              800
consePGIinTUNTDrakka      TGCATTCCCG TTTTATTTTC AAAAGTTGTT ACTGTCTCTA AATCAAGAAG
consensWesrPGI            TGCATTCCCG TTTTATTTTC AAAAGTTGTT ACTGTCTCTA AATCAAGAAG
consePGIintUNTR113        TGCATTCCCG TTTTATTTTC AAAAGTTGTC ACTGTCTCTA AATCAAGAAG
consePGIintUNTBrapaA      TGCATTCCCG TTTTATTTTC AAAAGTTGTC ACTGTCTCTA AATCAAGAAG
ConsePGIintUNTRRH1        TGCATTCCCG TTTTATTTTC AAAAGTTGTC ACTGTCTCTA AATCAAGAAG
PGIBo-EM:AF258277         .......... .......... .......... .......... ..........
PGIBra-EM:AF258278        .......... .......... .......... .......... ..........
consePGIintUNTBolera      TGCATTCCCG TTTTATTT.C AAAAGTTGTC CGGCCCCCTA AACCAAGAAG
consePGIintUNTR2000       TGCATTCCCG TTTTATTTTC AAAAGTTGTT ACTGTCTCTA AATCAAGAAG
Consensus                 tgcattcccg ttttattttc aaagttgt. actgtctcta aatcaagaag 801                                                              850
consePGIinTUNTDrakka      AAACCTTCTT AGTAGATCCA GCTGATATTC AGCCTTTTCT AAAATTGGACT
consensWesrPGI            AAACCTTCTT AGTAGATCCA GCTGATATTC AGCCTTTTCT AAAATTGGACT
consePGIintUNTR113        AAACCTTCTT AGTAGATCCA GTTGATATTC AGCCTTTTCT AAATTGGACT
consePGIintUNTBrapaA      AAACCTTCTT AGTAGATCCA G.TGATATTC AGCCTTTTCT AAAATTGGACT
ConsePGIintUNTRRH1        AAACCTTCTT AGTAGATCCA GTTGATATTC AGCCTTTTCT AAAATTGGACT
PGIBo-EM:AF258277         .......... .......... .......... .......... ..........
PGIBra-EM:AF258278        .......... .......... .......... .......... ..........
consePGIintUNTBolera      AAACCTTTCT AGGA...CCA GA....CTCC ACCCTTTTCT AAAATTGGACT
consePGIintUNTR2000       AAACCTTCTT AGTAGATCCA GCTGATATTC AGCCTTTTCT AAAATTGGACT
Consensus                 aaaccttctt agtagatcca g.tgatattc agcctttt.t aaattggact
                                                        18                  19
                          851                                                              900
consePGIinTUNTDrakka      GCAGGTTTTT AAA.GGGAGC TTCAAGCATT GATAAGCATT TCCAGTCCCC
consensWesrPGI            GCAGGTTTTT AAA.GGGAGC TTCAAGCATT GATAAGCATT TCCAGTCCAC
consePGIintUNTR113        GCAGGTTTTT AAA.GGGAGC TTCAAGCATT GATCAGCATT TCCAGTCC..
consePGIintUNTBrapaA      GCAGGTTTTT AAA.GGGAGC TTCAAGCATT GATCAGCATT TCCAGTCC..
ConsePGIintUNTRRH1        GCAGGTTTTT AAA.GGGAGC TTCAAGCATT GATCAGCATT TCCAGTCCAC
PGIBo-EM:AF258277         .......... .......... .......... .......... ..........
PGIBra-EM:AF258278        .......... .......... .......... .......... ..........
consePGIintUNTBolera      GCAGGTTTTT AAA.GGGGGC TTCAAGCATT GATAAGCATT TCCAGTCCAC
consePGIintUNTR2000       GCAGGTTTTT AAACGGGAGC TTCAAGCATT GATAAGCATT TCCAGTCCAC
Consensus                 gcaggttttt aaa.gggagc ttcaagcatt gat.agcatt tccagtcc.c
                                                                        20
                          901                                                              950
consePGIinTUNTDrakka      ACC.GTTTGA GAAGAATATA CCCGTGAGTT GCATTAGTTT GTGTGATTAT
consensWesrPGI            ACC.GTTTGA GAAGAATATA CCCGTGAGTT GCATTAGTT. GTGTGATTAT
consePGIintUNTR113        .CCCGTTTGA GAAGAATATA CCCGTGAGTT GCATTAGTT. ...GTGATTAT
consePGIintUNTBrapaA      .CCCGTTTGA GAAGAATATA CCCGTGAGTT GCATTAGTT. GTGTGATTAT
ConsePGIintUNTRRH1        ACC.GTTTGA GAAGAATATA CCCGTGAGTT GCATTAGTT. GTGTGATTAT
PGIBo-EM:AF258277         .......... .......... .......... .......... ..........
PGIBra-EM:AF258278        .......... .......... .......... .......... ..........
consePGIintUNTBolera      ACCCGTTTGA GAAGAATATA CCCGTGAGTT GCATTAGTT. GTGTGATTAT
consePGIintUNTR2000       ACC.GTTTGA GAAGAATATA CCCGTGAGTT GCATTAGTT. GTGTGATTAT
Consensus                 acc.gtttga gaagaatata cccgtgagtt gcattagtt. gtgtgattat
```

Figure 14 (d)

```
                       951                                                      1000
consePGIinTUNTDrakka   ACAGTTTTTC TTGTCTTTTT GCTATGCCCA TCAACACTAG AAGATTCGTG
       consensWesrPGI  ACAGTTTT.C TTGTCTTTT. GCTATGTCCA TCAACACTAG A.GATTCGTG
    consePGIintUNTR113 ACAGTTTT.C TTGCCTTTTT GCTAT..AGG GCAAC.CTAG A.GATTCATG
   consePGIintUNTBrapaA ACAGTTTT.C TTGTCTTTT. GCTATG.TCA TCAAC.CTAG A.GATTCATG
    ConsePGIintUNTRRH1 ACAGTTTT.C TTGTCTTTTT GCTAT...AT GCAACCCTAG ..GATTCATG
         PGIBo-EM:AF258277 .......... .......... .......... .......... ..........
         PGIBra-EM:AF258278 .......... .......... .......... .......... ..........
    consePGIintUNTBolera ACAGTTTT.C TTGTCTTTTT GCTAG..TGA TCAAC.CTAG A.GATTCGTG
   consePGIintUNTR2000 ACAGTTTT.C TTGTCTTTTT GCTATGTCCA TCAACACTAG A.GATTCGTG
             Consensus acagtttt.c ttgtctcttt gctat....a tcaac.ctag a.gattc.tg
                                                                              21

1001                                                     1050
consePGIinTUNTDrakka   AAGTTATTAG TGTAGCCAAC GCCTAGGGGG AGGTTGGTTG GCTGTTTTGG
       consensWesrPGI  AAGTTATTAG TGTAGTCAAC GCA....... .......... ..........
    consePGIintUNTR113 AAGTTATTAG TGTAGTCAAC GCAGAGGAGA G..TTCACTG ACGG......
   consePGIintUNTBrapaA AAGTTATTAG TGTAGTCAAC GCAGAGTGAG AGG.TGATTG ..........
    ConsePGIintUNTRRH1 AAGTTATTAG TGTAGTCAAC GCAGAGGAGG AGATGGTT.. ..........
         PGIBo-EM:AF258277 .......... .......... .......... .......... ..........
         PGIBra-EM:AF258278 .......... .......... .......... .......... ..........
    consePGIintUNTBolera AAGTTATTAG TGTAGTCAAC GCATAGGAGG AGC....... ..........
   consePGIintUNTR2000 AAGTTATTAG TGTAGTCAAC GCATAGGGAG AGGTGAT.GG TGACTTTTGG
             Consensus aagttattag tgtagtcaac gca.agg.g. .g........ ..........

1051            1076
consePGIinTUNTDrakka   ACGTTTTCAC GTGCTCCGGG GGGTTTTTGG GGACCAAACC CCCAAC
       consensWesrPGI  .......... .......... .......... .......... ......
    consePGIintUNTR113 .......... .......... .......... .......... ......
   consePGIintUNTBrapaA .......... .......... .......... .......... ......
    ConsePGIintUNTRRH1 .......... .......... .......... .......... ......
         PGIBo-EM:AF258277 .......... .......... .......... .......... ......
         PGIBra-EM:AF258278 .......... .......... .......... .......... ......
    consePGIintUNTBolera .......... .......... .......... .......... ......
   consePGIintUNTR2000 ACGATTTCAG GTGCTTTAGG GTTATTG... .......... ......
```

Figure 15 (a)

```
                     51                                                   100
      EMBH44836anti  .......... .......... .......... .......... ..........
   GCP18-5CP418L-Sams .......... .......... .......... .......... ..........
    GCP18-2CP418L-Wes .......... .......... .......... .......... ..........
  GCP18-4CP418L-R2000 .......... .......... .......... ........ CP418L ...
      conse129bal-Drak .......... .......... AAACAAATCA AAATTCTAAA TTTCTCCA
    GCPS18-129Sam-ba2 ...... . AAAC TATGTA ACAAAAATCA AAATTGTAAA TGTCTCCA
   GCPR18-3129R211-ba2 ..... ..... AA CCAAAAATCC AAATTGTAAA TGTTCCCT.
    GCP18-10129R20-ba2 .......... .......... CAAAATCCA AAATTGTAAA TGTC.CCT
             Consensus .......... .......... .......... .......... ..........

101                                                  150
      EMBH44836anti  .......... .......... .......... .......... ..........
   GCP18-5CP418L-Sams .......... .......... ........AT A.CATTTTCT GTAA
    GCP18-2CP418L-Wes .......... .......... .AGG T.AT A.CATTTTCT GTAA
  GCP18-4CP418L-R2000 .......... .......... .AGG TCAT A.CATTTTCT GTAA
      conse129bal-Drak TCACAAGGAC CTACAGAATA GAGTTATCAT AACATTT CT GTAA
    GCPS18-129Sam-ba2 TCGTAACGAC ..TACAGAATA GAGTTATCAT AACATTTTCT G AA
   GCPR18-3129R211-ba2 TGGTAACGGC CTCAAAAA.A GAGGTATCAA AAC.TTTTCT GT.A
    GCP18-10129R20-ba2 TGGTTACCGC C.CAAAAA.A AAGGT...CAA AACTT.TCCG GTAA
             Consensus .......... .......... .......... .......... ..........

151                                                  200
      EMBH44836anti  .......... .......... .......... .......... ..........
   GCP18-5CP418L-Sams .TATTTCCAT CAAAATGA.. .CTAGAGAAC AGCAGTTCTT ATAACATTAT
    GCP18-2CP418L-Wes .TATTTCCAT CAAAATGA.. .CTAGAGAAC AG.AGTTCTT ATAACATTAT
  GCP18-4CP418L-R2000 ATATTTCCAT CAAAATGA.. .CTAGAGAAC AG.AGTTCTT ATAACATTAT
      conse129bal-Drak ATATTTCCAT CAAAATGA.. .CTAGAGAAC AG.AGTTCTT ATAACATTAT
    GCPS18-129Sam-ba2 ATGTTTCCAT CAAAATGA CTATCGAAC ATAATTAAT ATA.CATTTT
   GCPR18-3129R211-ba2 ATGTTTCCAT CAAAATG. CTATCGGAC ATAATTAAT ATAAC.TTCT
    GCP18-10129R20-ba2 ATGTTTCCAT CAAAATG. CTTCGGA.C ATAATTAAT ATAAC.TTCT
             Consensus ATGTTTCCCT CAAA.TGG CTTCGGA.C ATAATTAAA A...CATTCT 201                                                  250
      EMBH44836anti  .......... .......... .......... .......... ..........
   GCP18-5CP418L-Sams CTGTAAA TG.TTCCAA CAAAA CCACT ACATAGCAGAGTTC .TTATAACAT
    GCP18-2CP418L-Wes CTGTAAA TG.TTCCAA CAAAA CCACT ACATAGCAGAGTTC ATTATAACAT
  GCP18-4CP418L-R2000 CTGTAAA TG.TTCCAA CAAAA CCACT ACATAGCAGAGTTC .TTATAACAT
      conse129bal-Drak CTGTAAA TG.TTCCAA CAAAA CCACT ACATAGCAGAGTTC .TTATAACAT
    GCPS18-129Sam-ba2 CTG.AAAAT AATTCCCCT CAAAAATTA. .CATT TTC TTACAA.A.
   GCPR18-3129R211-ba2 CTG.AAAAT.ATTCCCT CAAAA TTA. ACATT TTC T.ACAA.A.
    GCP18-10129R20-ba2 CTG.AAA.TAATTCCCT CAAAA TTA. ACAT. TTC T.ACAA.A.
             Consensus ---------- ---------- ---------- ---------- ----------

251                                                  300
      EMBH44836anti  .......... .......... .......... .......... ...CTATACC
   GCP18-5CP418L-Sams TGTCTGT.AA ATGTCCAATC AAAACCACTA CAGAACAAAG CTCCTATAAC
    GCP18-2CP418L-Wes TGTCTGT.AA ATGTCCAATC AAAACCACTA CAGAACAAAG CTCCTATAAC
  GCP18-4CP418L-R2000 TGTCTGT.AA ATGTCCAATC AAAACCACTA CAGAACAAAG CTCCTATAAC
      conse129bal-Drak TGTCTGT.AA ATGTCCAATC AAAACCACTA CAGAACAAAG CTCCTATAAC
    GCPS18-129Sam-ba2 TGTTTC... .......... .......... CATCAAAATG AGACTCCA.G
   GCPR18-3129R211-ba2 TGTTTC... .......... .......... CATCAAAATG AGACTACA.G
    GCP18-10129R20-ba2 TGTTTC... .......... .......... CATCAAAATG AGACTACA.G
             Consensus tttctgt.aa tgtttccatc aaaatgacta cgaacataa ttaatAtaac 301                                                  350
      EMBH44836anti  A TTGTTT ATACAAAGTT TCACT AAAT CTACAAACTT CCCCCGTAAA
   GCP18-5CP418L-Sams A TTGTTT ATACAAGTTT .CACT AAAT CTACAAACTT TCCCCGTAAA
    GCP18-2CP418L-Wes A TTGTTT ATACAAAGTT TCACT AAAT CTACAAACTT TCCCCGTAAA
  GCP18-4CP418L-R2000 A TTGTTT ATACAAGTTT .CACT AAAT CTACAAACTT TCCCCGTAAA
      conse129bal-Drak A. TGTTT ATACAAAGTT TCACT AAAT CTACAAACTT TCCCCGTAAA
    GCPS18-129Sam-ba2 AAC.CAGTTC TTGCATAGTT TCACTTAAAT CTACAAACTT TC........
   GCPR18-3129R211-ba2 AACACAGTTC TTGCATAGTT TCACT.AAAT CTACAAACTT TC........
    GCP18-10129R20-ba2 A.CCCAGTTC TTGCATAGTT TC.CT.AAAT CTTCAAACTT TC........
             Consensus ---------- ---------- ---------- ---------- ----------
```

Figure 15 (b)

```
                        351                                                    400
         EMBH44836anti  TGAGCTTAAT ATCACCCAA. GATGTTTCA ATCAGAT AAA GAGTAACGAC
      GCP18-5CP418L-Sams TGAGCTTAAT ATCACCCAAA GATGTTTCA ATCAGAT AAA GAGTAACGAC
       GCP18-2CP418L-Wes TGAGCTTAAT ATCACCCAAA GATGTTTCA ATCAGAT AAA GAGTAACGAC
      GCP18-4CP418L-R2000 TGAGCTTAAT ATCACCCAAA GATGTTTCA ATCAGAT AAA GAGTAACGAC
         conse129bal-Drak TGAGCTTAAT ATCACCCAAA GATGTTTCA ATCAGAT AAA GAGTA.CGAC
        GCPS18-129Sam-ba2 [.......]AAT CTTATCTAAA G.TTATCAC ATCACAT GAA GA[......]
       GCPR18-3129R211-ba2 [.......]AAT CTTATCTAA. G.TTATCAC ATCACAT GAA GA[......]
       GCP18-10129R20-ba2 [.......]AAT CTTATCTAAA G.TTATCAC ATCACAT GAA GA[......]
              Consensus  ---------- ---------- --------- ------- --- ----------

401
         EMBH44836anti  ATCGTTTTGA GATTAGAACA AA
      GCP18-5CP418L-Sams ATCGTTTTGA GATTAGAACA AA
       GCP18-2CP418L-Wes ATCGTTTTGA GATTAGAACA AA
      GCP18-4CP418L-R2000 ATCGTTTTGA GATTAGAACA AA
         conse129bal-Drak ATCGTTTTGA GATTAGAACA AA
        GCPS18-129Sam-ba2 [.... .......... .GAGC AA]
       GCPR18-3129R211-ba2 [.... .......... ..GGC AA]
       GCP18-10129R20-ba2 [.... .......... ..GGC A.]
              Consensus 431                                                    480
         EMBH44836anti  CTGAAACTTA CGTAGAGTGA TTTGAGGAGT AGGCTCGTTG CCAGCAGAGC
      GCP18-5CP418L-Sams CTGAAACTTA CGTAGAGTGA TTTGAGGAGT AGGCTCGTTG CCAGCAGAGC
       GCP18-2CP418L-Wes CTGAAACTTA CGTAGAGTGA TTTGAGGAGT AGGCTCGTTG CCAGCAGAG.
      GCP18-4CP418L-R2000 CTGAAACTTA CGTAGAGTGA TTTGAGGAGT AGGCTCGTTG CCAGCAGAGC
         conse129bal-Drak CTGAAACTTA CGTAGAGTGA TTTGAGGAGT AGGCTCGTTG CCAGCAGAGC
        GCPS18-129Sam-ba2 GTAAACTTA CCTAGAGTGA TCTGAGGAGT AGGCTCGTTG CCAGCGGAGC
       GCPR18-3129R211-ba2 GTAAACTTA CCTAGAGTGA TCTGAGGAGT AGGCTCGTTG CCAGCGGAGC
       GCP18-10129R20-ba2 GTA.CCTTA CCTAGAGTGA TCTGAGGAGT AGGCTCGTTG CCAGCGGAGC
              Consensus  .t.aa.ctta c.tagagtga t.tgaggagt aggctcgttg ccagc.gagc 481                                                    530
         EMBH44836anti  TAGCTCTCTC CTCCGCCTCA TGAAGCATCT GTTGCACCTG AGACAACCGT
      GCP18-5CP418L-Sams TAGCTCTCTC CTCCGCCTCA TGAAGCATCT GTTGCACCTG AGACAACCGT
       GCP18-2CP418L-Wes TAGCTCTCTC CTCCGCCTCA TGAAGCATCT GTTGCACCTG AGACAACCGT
      GCP18-4CP418L-R2000 TAGCTCTCTC CTCCGCCTCA TGAAGCATCT GTTGCACCTG AGACAACCGT
         conse129bal-Drak TAGCTCTCTC CTCCGCCTCA TGAAGCATCT GTTGCACCTG AGACAACCGT
        GCPS18-129Sam-ba2 TAGCTCTCTC CTCC.CCTCA TGAAGCATCT GCTGCACCTG AGACAACCGT
       GCPR18-3129R211-ba2 TAGCTCTCTC CTCCGCCTCA TGAAGCATCT GCTGCACCTG AGACAACCGT
       GCP18-10129R20-ba2 TAGCTCTCTC CTCCGCCTCA TGAAGCATCT GCTGCACCTG AGACA.CCGT
              Consensus  tagctctctc ctccgcctca tgaagcatct g.tgcacctg agacaaccgt 531                                                    580
         EMBH44836anti  GACGAAACTT TCCGATCACC GCCACCAGAA TTCGACGCCG CGCATCGGAA
      GCP18-5CP418L-Sams GACGAAACTT TCCGATCACC GCCACCAGAA TTCGACGCCG CGCATCGGAA
       GCP18-2CP418L-Wes GACGAAACTT TCCGATCACC GCCACCAGAA TTCGACGCCG CGCATCGGAA
      GCP18-4CP418L-R2000 GACGAAACTT TCCGATCACC GCCACCAGAA TTCGACGCCG CGCATCGGAA
         conse129bal-Drak GACGAAACTT TCCGATCACC GCC.CCAGAA TTCGACGCCG CGCATCGGAA
        GCPS18-129Sam-ba2 GACGAAACTT TCCGATCACC GCCACCAGAA TTCGACGCCG CGCATCGGAA
       GCPR18-3129R211-ba2 GACGAAACTT TCCGATCACC GCCACCAGAA TTCGACGCCG CGCATCGGAA
       GCP18-10129R20-ba2 GACGAAACTT TCCGATCCCC GCC.CCAGAA TTCGACGCCG CGCATCGGAA
              Consensus  gacgaaactt tccgatcacc gccaccagaa ttcgacgccg cgcatcggaa 581                                                    630
         EMBH44836anti  GGATCCGAAT CGGGAACTGG AGTGAACCCG AGCGATCCCG GGAGTGCGAC
      GCP18-5CP418L-Sams GGATCCGAAT CGGGAACTGG AGTGAACCCG AGCGATCCCG GGAGTGCGAC
       GCP18-2CP418L-Wes GGATCCGAAT CGGGAACTGG AGTGAACCCG AGCGATCCCG GGAGTGCGAC
      GCP18-4CP418L-R2000 GGATCCGAAT CGGGAACTG. AGTGAACCCG AGCGATCCCG GGAGTGCGAC
         conse129bal-Drak GGATCCGAAT CGGGAACTGG AGTGAACCCG AGCGATCCCG GGAGTGCGAC
        GCPS18-129Sam-ba2 GGATCCGAAT CGGGAACTGG AGTGAACCAG AGCGATCCCG GGAGTGCGAC
       GCPR18-3129R211-ba2 GGATCCGAAT CGG.AACTGG AGTGAACCAG AGCGATCCCG GGAGTGCGAC
       GCP18-10129R20-ba2 GGATCCGAAT CGGGAACTGG AGTGAACCAG AGCGATCCCG GGAGTGCGAC
              Consensus  ggatccgaat cgggaactgg agtgaacc.g agcgatcccg ggagtgcgac
```

Figure 15 (c)

```
                        631                                                          690
      EMBH44836anti    GGAGCGATGG  GAAAAGAGAG  TGGCACGATT  TCGACGAAGA  GTGGAAGAGG
    GCP18-5CP418L-Sams GGAGCGATGG  GAAAAGAGAG  TGGCACGATT  TCGACGAAGA  GTGGAAGAGG
     GCP18-2CP418L-Wes GGAGCGATGG  GAAAAGAGAG  TGGCACGATT  TCGACGAAGA  GTGGAAGAGG
   GCP18-4CP418L-R2000 GGAGCGATGG  GAAAAGAGAG  TGGCACGATT  TCGACGAAGA  GTGGAAGAGG
       conse129ba1-Drak GGAGCGATGG  GAAAAGAGAG  TGGCACGATT  TCGACGAA.A  GTGGAAGAGG
     GCPS18-129Sam-ba2  GGAGCGTTGG  AAAAAGAGAG  TGGCACGATT  TCGACGAAGA  GAGGAAGAGG
    GCPR18-3129R211-ba2 GGAGCGTTGG  AAAAAGAGAG  TGGCACGATT  TCGACGAAGA  GAGGAAGAGG
     GCP18-10129R20-ba2 GGAGCGTTGG  AAAAAGAGAG  TGGCACGATT  TCG.CGAAGA  GAGGAAGAGG
              Consensus ggagcg.tgg  .aaaagagag  tggcacgatt  tcgacgaaga  g.ggaagagg 691                                                          740
      EMBH44836anti    AGAGGGTGGT  GGATAAACTC  GCGTATGATC  AAGTTCGTCA  TCGTCCTGAT
    GCP18-5CP418L-Sams AGAGGGTGGT  GGATAAACTC  GCGTATGATC  AAGTTCGTCA  TCGTCCTGAT
     GCP18-2CP418L-Wes AGAGGGTGGT  GGATAAACTC  GCGTATGATC  AAGTTCGTCA  TCGTCCTGAT
   GCP18-4CP418L-R2000 AGAGGGTGGT  GGATAAACTC  GCGTATGATC  AAGTTCGTCA  TCGTCCTGAT
       conse129ba1-Drak AGAGGGTGGT  GGATAAACTC  GCGTATGATC  AAGTTCGTCA  TCGTCCTGAT
     GCPS18-129Sam-ba2  AGAGGGTGGT  GGATAAACTC  GCGTATGATC  AAGTTCGTCA  TCGTCCTGAT
    GCPR18-3129R211-ba2 AGAGG.TGGT  GGATAAACTC  GCGTATGATC  AAGTTCGTCA  TCGTCCTGAA
     GCP18-10129R20-ba2 AGAGGGTGGT  GGATAAACTC  GCGTATGATC  AAGTTCGTCA  TCGTCCTGAA
              Consensus agagggtggt  ggataaactc  gcgtatgatc  aagttcgtca  tcgtcctga.

741                              pSG129antiU 790            800
      EMBH44836anti    TGCCGCCATT  TTTTTTGTCA  GGGCGCTCTG  TGGCTTAGAA  GTTTCCGATG
    GCP18-5CP418L-Sams TGCCGCCATT  TTTTTTGTCA  GGGCGCTCTG  TGGCTTAGAA  GTTTCCGATG
     GCP18-2CP418L-Wes TGCCGCCATT  TTTTTTGTCA  GGGCGCTCTG  TGGCTTAGAA  GTTTCCGATG
   GCP18-4CP418L-R2000 TGCCGCCATT  TTTTTTGTCA  GGGCGCTCTG  TGGCTTAGAA  GTTTCCGTG.
       conse129ba1-Drak TGCCGCCATT  TTTTTTGTCA  GGGCGCTCTG  .GGCTTAGAA  GTTTCCGA..
     GCPS18-129Sam-ba2  TGCCGCCATT  CTTGTTCAC.  .GGCGCTCTG  GGT.......  ..........
    GCPR18-3129R211-ba2 TGCCGCC...  ..........  ..........  ..........  ..........
     GCP18-10129R20-ba2 TGCC..CAT.  CTTGAGCTC.  .GG.GCGCGG  GCTCACAA..  ..........
              Consensus tgccgccat.  .tt.....c.  .gg.gc.c.g  ..........  ..........

791
      EMBH44836anti    TCAATGAAC   A GTGACACGAC  GAAATGC
    GCP18-5CP418L-Sams TCAATGAAAC  AGAAT...TC  CGGG...
     GCP18-2CP418L-Wes CCAATGAACA  AGATTATTTC  CGATG..
   GCP18-4CP418L-R2000 ..........  ..........  .......
       conse129ba1-Drak ..........  ..........  .......
```

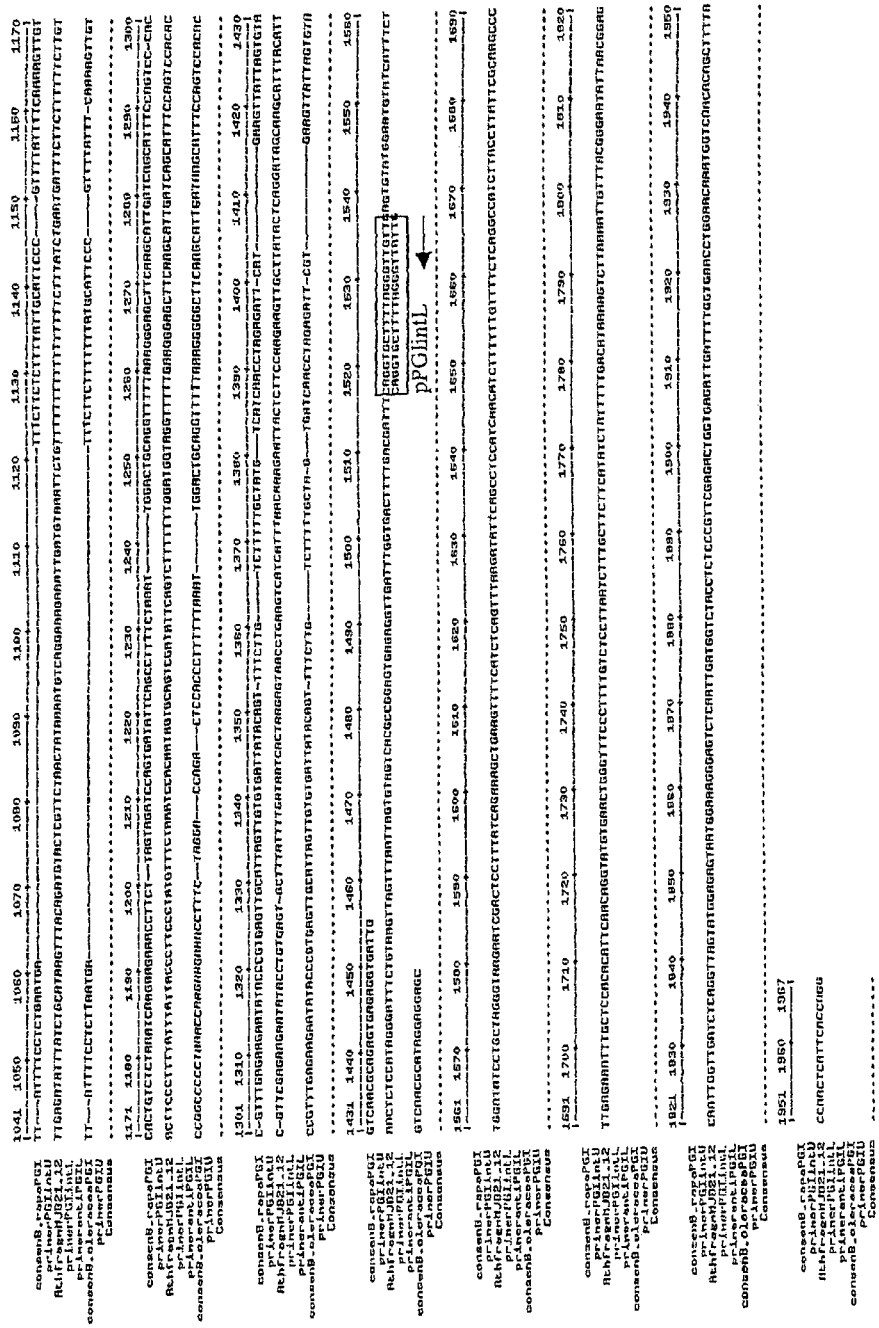
Figure 16 BIS

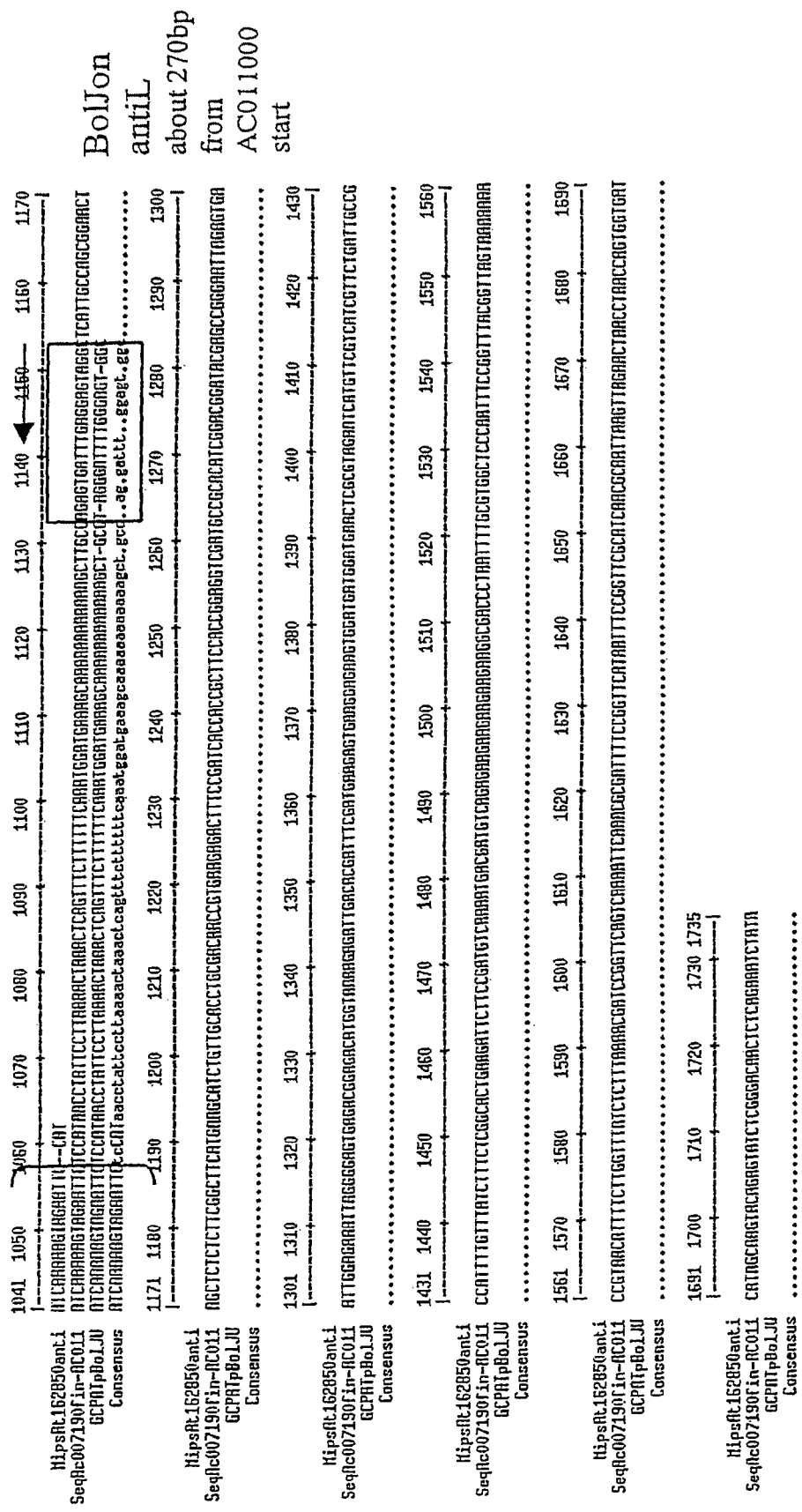
Figure 17 BIS

METHOD OF PRODUCING DOUBLE LOW RESTORER LINES OF *BRASSICA NAPUS* HAVING A GOOD AGRONOMIC VALUE

CROSS-REFERENCE TO RELATED APPLICATIONS

This application is a continuation, of United States Application No. 10/563,277, filed on Jul. 13, 2006, which is a national phase entry under 35 U.S.C. §371 of International Application No. PCT/IB04/02491 filed Jul. 5, 2004, which claims priority under 35 USC 119(d) to European Application no. 03293057.0 filed Dec. 8, 2003 and European Application No. 03291677.7 filed Jul. 4, 2003, all of which are incorporated herein by reference.

BACKGROUND OF THE INVENTION

Breeding restorer lines for the Ogu-INRA Cytoplasmic Male Sterility (cms) system in rapeseed (*Brassica napus L.*) has been a major objective during the past few years. Extensive backcross and pedigree breeding were necessary to improve their female fertility and to get double low restorer lines. The so-called double <<low >> varieties are those low in erucic acid in the oil and low in glucosinolates in the solid meal remaining after oil extraction. However some difficulties can still be encountered in breeding these lines (introgression rearrangements, possible linkage with negative traits) due to the large size of the radish introgression.

The inventors thus assigned themselves the objective of providing a new improved double low restorer line with a good agronomic value.

This objective is obtained by a new method of producing a recombined double low restorer line for the Ogu-INRA cms in rapeseed.

SUMMARY OF THE INVENTION

A first object of the present invention relates to a method of producing double low restorer lines of *Brassica napus* for Ogura cytoplasmic male sterility (cms) presenting radish introgression carrying the Rfo restorer gene deleted of the radish Pgi-2 allele and recombined with the Pgi-2 gene from *Brassica oleracea*, and having a good agronomic value characterized by female fertility, a good transmission rate of Rfo and a high vegetative vigor, said method including the step of:
a) crossing double low cms lines of spring *Brassica napus* comprising a deleted radish insertion with the double low line of spring Drakkar for forming heterozygous restored plants of *Brassica napus*,
b) irradiating before meiosis the heterozygous restored plants obtained in step a) with gamma ray irradiation,
c) crossing pollen from flowers obtained in step b) with the cms double low spring Wesroona line,
d) testing the progeny for vigor, female fertility and transmission rate of the cms gene,
e) selecting progeny lines.

In the present invention, the term "lines(s)" means a plant which is essentially homozygote and which is reproducible by auto-pollination.

The above method, wherein the irradiation dose in step b) is 65 Gray during 6 nm.

According to one advantageous form of embodiment of the method of the present invention, the irradiation dose in step b) is 65 Gray during 6 nm.

According to one advantageous form of embodiment of the method according to the present invention, the double low cms line of spring *Brassica napus* of step a) is R211.

R211 is an INRA spring restorer line.

Drakkar is a French spring registered variety.

Wesroona is an Australian spring registered variety.

According to one advantageous form of embodiment of the method according to the present invention, the testing in step d) is performed with the combination of five markers selected from PGIol, PGIUNT, PGIint, BolJon and CP418.

Another object of the present invention relates to double low restorer lines of *Brassica napus* for Ogura cms presenting a Rfo insertion deleted of the radish Pgi-2 allele and recombined with the Pgi-2 gene from *Brassica oleracea*, and having a good agronomic value characterized by female fertility, a good transmission rate of Rfo and a high vegetative vigor.

According to one advantageous form of embodiment, the double low restorer lines present a unique combination of five markers selected from PGIol, PGIUNT, PGIint, BolJon and CP418.

Another object of the present invention relates to *Brassica napus* hybrid plants and progeny thereof obtained though the steps of:
a) providing a restorer line produced according to the above method and bred to be homozygous,
b) using said restorer line in a hybrid production field as the pollinator,
c) using cms sterile plants in a hybrid production field as the hybrid seed producing plant, and
d) harvesting the hybrid seed from the male sterile plant.

Another object of the present invention relates to seeds of *Brassica* plant obtained from the methods according to the present invention.

Still another object of the invention relates to seeds of *Brassica napus* deposited in NCIMB Limited, 23 St Machar Drive, Aberdeen, Scotland, AB24 3RY, UK, on Jul. 4, 2003, under the reference number NCIMB41183.

Another object of the present invention relates to the use of at least four markers PGIol, PGIint, BolJon and CP418, or any portion of them comprising at least one polymorphic site, for characterizing recombined restorer lines of *Brassica napus* for Ogura cms presenting a Rfo insertion deleted of the radish Pgi-2 allele and recombined with the Pgi-2 gene from *Brassica oleracea*, and having a good agronomic value characterized by female fertility, a good transmission rate of Rfo and a high vegetative vigor.

In a preferred embodiment, the combination is of five markers PGIol, PGIUNT, PGIint, BolJon and CP418.

In the present invention, the expression "any portion of them comprising at least one polymorphic site" means any part of the sequence showing at least a difference between the *B.oleracea* type sequence and *B.rapa* type sequence. Such markers are represented in the following figures and sequence listing for the R2000 line, a double low restorer lines of *Brassica napus* for cms according to the present invention.

According to one advantageous form of embodiment, the present invention relates to:

The marker PGIol which is amplified using the primers:

```
PGIol U and PGIol L
(PGIol U:
5'TCATTTGATTGTTGCGCCTG3';      (SEQ ID NO: 6)

PGIol L:
5'TGTACATCAGACCCGGTAGAAAA3'    (SEQ ID NO: 7))
```

The marker PGIint which is amplified using the primers:

```
PGIint U and PGIint L
(PGIint U:
5'CAGCACTAATCTTGCGGTATG3';      (SEQ ID NO: 8)

PGIint L:
5'CAATAACCCTAAAAGCACCTG3'       (SEQ ID NO: 9))
```

The marker PGIUNT which is amplified using the primers:

```
PGIol U and PGIint L:
(PGIol U:
5'TCATTTGATTGTTGCGCCTG3';       (SEQ ID NO: 10)

PGIint L:
5'CAATAACCCTAAAAGCACCTG3'       (SEQ ID NO: 11))
```

The marker BolJon which is amplified using the primers:

```
BolJon U and BolJon L:
(BolJon U:
5'GATCCGATTCTTCTCCTGTTG3';      (SEQ ID NO: 12)

BolJon L:
5'GCCTACTCCTCAAATCACTCT3'       (SEQ ID NO: 13))
```

The marker CP418 which is amplified using the primers:

```
SG129 U and pCP418 L: SG129 U: cf Giancola et
al, ( 2003 Theor Appl. Genet. (in press)
pCP418 L:
5'AATTTCTCCATCACAAGGACC3')      (SEQ ID NO: 14)
```

Another object of the present invention relates to the PGIol, PGIUNT, PGIint, BolJon and CP418 markers whose sequences follow:

```
PGIol R2000 marker:                                 (SEQ ID NO: 1)
TCATTTGATTGTTGCGCCTGTCGCCTTGTTGTGTTATGATGAATGAACAGCAGTCATTTA     60

ACATGTGGTTAACTTAACAGGGCTCCGGCTGTTGCAAAACACATGGTTGCTGTCAGCACT    120

AATCTTGCGGTATGAATTTGTGATTAAATTTGTTTGTTTGTGACTCTTTCTTCATTGTTC    180

GTTTTCGTACAATAAACCGAATGTATAATCTTTTTACAAACTGAATTTTCTACCGGGTCT    240

GATGTACA                                                        248

PGIUNT R2000 marker:                                (SEQ ID NO: 2)
TCATTTGATTGTTGCGCCTGTCGCCTTGTTGTGTTATGATGAATGAACAGCAGTCATTTA     60

ACATGTGGTTAACTTAACAGGGCTCCGGCTGTTGCAAAACACATGGTTGCTGTCAGCACT    120

AATCTTGCGGTATGAATTTGTGATTAAATTTGTTTGTTTGTGACTCTTTCTTCATTGTTC    180

GTTTTCGTACAATAAACCGAATGTATAATCTTTTACAAACTGAATTTTCTACCGGGTCTG    240

ATGTACAATGCTAGTCTCCATGTTCTTGGGGATCATGATTTATTTTCTACATGTATTCAG    300

ACAGTACAGAAGAAAGTGTTCAAAACTCTGGATGTTTTAATTTACAGTTAGTGGAGAAGT    360

TCGGCATTGATCCGAACAATGCATTTGCATTTTGGGACTGGGTTGGTGGAAGGTACAGTG    420

GTAAGTGCTTGTTTATTTGGTTGTATAAATTTCTCGTCCATTTCCGCTTGCTTAGTGTAT    480

AACTGAAATTCTTTTGCAGTTTGCAGTGCTGTTGGAGTCTTACCATTGTCTCTACAGTAT    540

GGCTTCTCTGTGGTTGAGAAGTACGGTACCTTCTACTTTATCAGCCATCTCATAAAATGT    600

CTTAGGCATATTCTTTCTATTTTATTTCCCTCTTAATGATTTCTTCTTTTTTTATTGCA    660

GATCCAGCTGATATTCAGCCTTTTTAAATTGGACTGCAGGTTTTTAAAGGGGAGCTTCA    780

AGCATTGATAAGCATTTCCAGTCCACACCGTTTGAGAAGAATATACCCGTGAGTTGCATT    840

AGTTGTGTGATTATACAGTTTTCTTGTCTTTTTGCTATGTCCATCAACACTAGAGATTCG    900

TGAAGTTATTAGTGTAGTCAACGCATAGGGAGAGGTGATTGGTGACTTTTGGACGATTTC    960

AGGTGCTTTAGGGTTATTG                                             979

PGIint R2000 marker:                                (SEQ ID NO: 3)
CAGCACTAATCTTGCGGTATGAATTTGTGATTAAATTTGTTTGTTTGTGACTCTTTCTTC     60

ATTGTTCGTTTTCGTACAATAAACCGAATGTATAATCTTTTACAAACTGAATTTTCTACC    120

GGGTCTGATGTACAATGCTAGTCTCCATGTTCTTGGGGATCATGATTTATTTTCTACATG    180

TATTCAGACAGTACAGAAGAAAGTGTTCAAAACTCTGGATGTTTTAATTTACAGTTAGTG    240

GAGAAGTTCGGCATTGATCCGAACAATGCATTTGCATTTTGGGACTGGGTTGGTGGAAGG    300

TACAGTGGTAAGTGCTTGTTTATTTGGTTGTATAAATTTCTCGTCCATTTCCGCTTGCTT    360
```

-continued

```
AGTGTATAACTGAAATTCTTTTGCAGTTTGCAGTGCTGTTGGAGTCTTACCATTGTCTCT      420

ACAGTATGGCTTCTCTGTGGTTGAGAAGTACGGTACCTTCTACTTTATCAGCCATCTCAT      480

AAAATGTCTTAGGCATATTCTTTCTATTTTATTTCCCTCTTAATGATTTCTTCTTTTTTT      540

TATTGCATTCCCGTTTTATTTTCAAAAGTTGTTACTGTCTCTAAATCAAGAAGAAACCTT      600

CTTAGTAGATCCAGCTGATATTCAGCCTTTTTTAAATTGGACTGCAGGTTTTTAAAGGGG      660

AGCTTCAAGCATTGATAAGCATTTCCAGTCCACACCGTTTGAGAAGAATATACCCGTGAG      720

TTGCATTAGTTGTGTGATTATACAGTTTTCTTGTCTTTTTGCTATGTCCATCAACACTAG      780

AGATTCGTGAAGTTATTAGTGTAGTCAACGCATAGGGAGAGGTGATTGGTGACTTTTGGA      840

CGATTTCAGGTGCTTTAGGGTTATTG                                        866

BolJon R2000 marker:                         (SEQ ID NO: 4)
GATCCGATTCTTCTCCTGTTGAGATCAGCTCCAAACATCAAACAACTTGTACACAAATAT      60

CTTTACTTGCTAAATGGAACATGACAAGAGATAGAAAATCTTGCTCATAGTATTGTACAA     120

GGGATAACAGTGTAGAAAACAAACCGTCTGTAAGATTTTCTCCCTGATCCTCTCACTTAA     180

CCAGTAGGCGTTTTTCACATTGAAGCGCATATCTACTTTGGTATTCACTGAATAAAAAAA     240

GAAAGCTGGTAACATGTGAAGGATATACAAGCATTGATACACCAAGTAGTCACAAACTAC     300

ATTATAAAGGTCAGACCTTTGTTCACATTCTGGCCTCCAGGACCACCGCTTCTAGCAAAG     360

TTAAGCGTAACATGGTCTGCACGTATACAAATGAAAATGTTTCTATCAAAATCCTATAAA     420

ATAGAGCTCTATAACATTGTCGATACATAGTTTCACTAACTCTGCAAGTACTAAACACAT     480

ATACAAACAAAACTATGCGAACAGATCAAAACTACTACAGAACACAGTTCTATGACACTG     540

TCGATAGTAACATCCTCTGCAAGTACCAAAGAGATAGCAAATGAAACTATGTAAACAAAT     600

CAAAATTCTAAATTTCTCCATCACAAGGACCTACAGAATAGAGTTATCATAACATTTTCT     660

GTAAATATTTCCATCAAAATGACTAGAGAACAGAGTTCTTATAACATTATCTGTAAATGT     720

TCCAACAAAACCACTACATAGCAGAGTTCTTATAACATTGTCTGTAAATGTCCAATCAAA     780

ACCACTACAGAACAAAGCTCCTATAACATTGTTTATACAAAGTTTCACTAAATCTACAAA     840

CTTTCCCCGTAAATGAGCTTAATATCACCCAAAGATGTTTCAATCAGATAAAGAGTACGA     900

CATCGTTTTGAGATTAGAACAAACTGAAACTTACGTAGAGTGATTTGAGGAGTAGGC       957

CP418L R2000 marker:                         (SEQ ID NO: 5)
AATTTCTCCATCACAAGGACCTACAGAATAGAGTTATCATAACATTTTCTGTAAATATTT      60

CCATCAAAATGACTAGAGAACAGAGTTCTTATAACATTATCTGTAAATGTTCCAACAAAA     120

CCACTACATAGCAGAGTTCTTATAACATTGTCTGTAAATGTCCAATCAAAACCACTACAG     180

AACAAAGCTCCTATAACATTGTTTATACAAAGTTTCACTAAATCTACAAACTTTCCCCGT     240

AAATGAGCTTAATATCACCCAAAGATGTTTCAATCAGATAAAGAGTAACGACATCGTTTT     300

GAGATTAGAACAAACTGAAACTTACGTAGAGTGATTTGAGGAGTAGGCTCGTTGCCAGCA     360

GAGCTAGCTCTCTCCTCCGCCTCATGAAGCATCTGTTGCACCTGAGACAACCGTGACGAA     420

ACTTTCCGATCACCGCCACCAGAATTCGACGCCGCGCATCGGAAGGATCCGAATCGGGAA     480

CTGAGTGAACCCGAGCGATCCCGGGAGTGCGACGGAGCGATGGGAAAAGAGAGTGGCACG     540

ATTTCGACGAAGAGTGGAAGAGGAGAGGGTGGTGGATAAACTCGCGTATGATCAAGTTCG     600

TCATCGTCCTGATTGCCGCCATTTTTTTTGTCAGGGCGCTCTGTGGCTTAGAAGTTTCCG     660

ATGTCAATGAAC                                                     672
```

BRIEF DESCRIPTION OF THE DRAWINGS

In the annexed drawing that follows, the following abbreviations are used:

| | |
|---|---|
| Dra | Drakkar |
| Rel-15-1, E38, R15 | R2000 |
| Hete, Hel, R211.Drakkar | heterozygous R211 * Drakkar, |
| Darm | Darmor |
| Bol: | *Brassica oleracea* |
| Bra, B.rap: | *Brassica rapa* |
| GCPA18-A19, Wes, Aust: | Wesroona |
| Sam, SamlPGIolSunt5 | Samourai |
| RRH1, ba2c | RRH1 |
| rav, N.WR | Hybrid *Brassica napus* * wild Radish |

Figure 1:
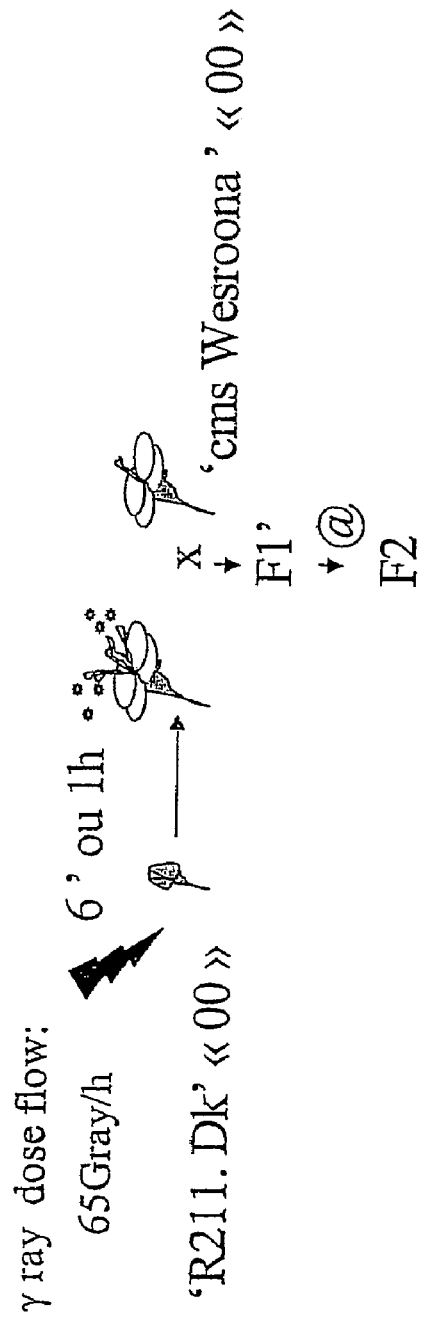

FIG. 1 illustrates Gamma ray Iradiation and F2 production.

Figure 2:
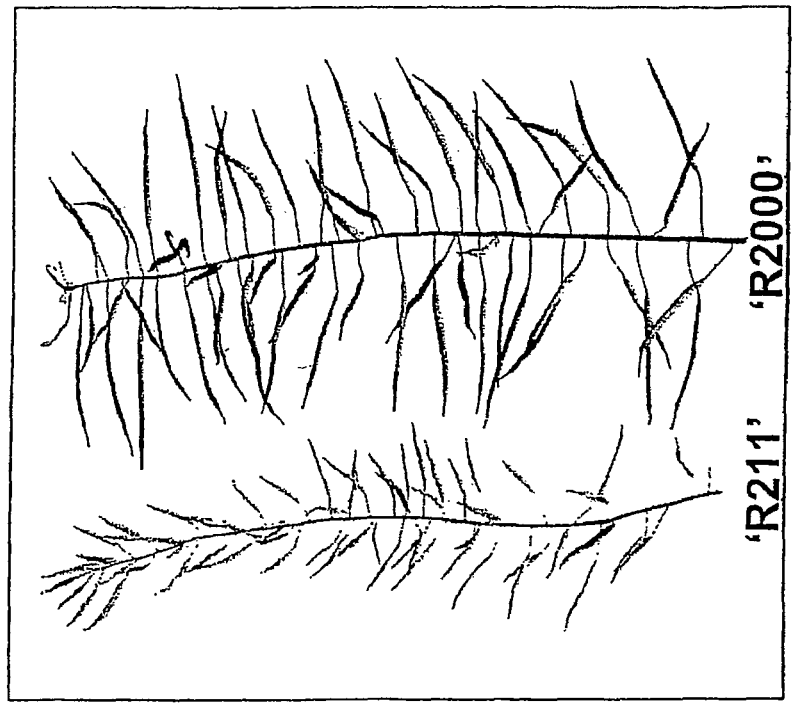

FIG. 2 illustrates seed set on 'R211' and 'R2000'.

FIG. 3 illustrates the number of seeds per pod of different lines.

Figure 4:
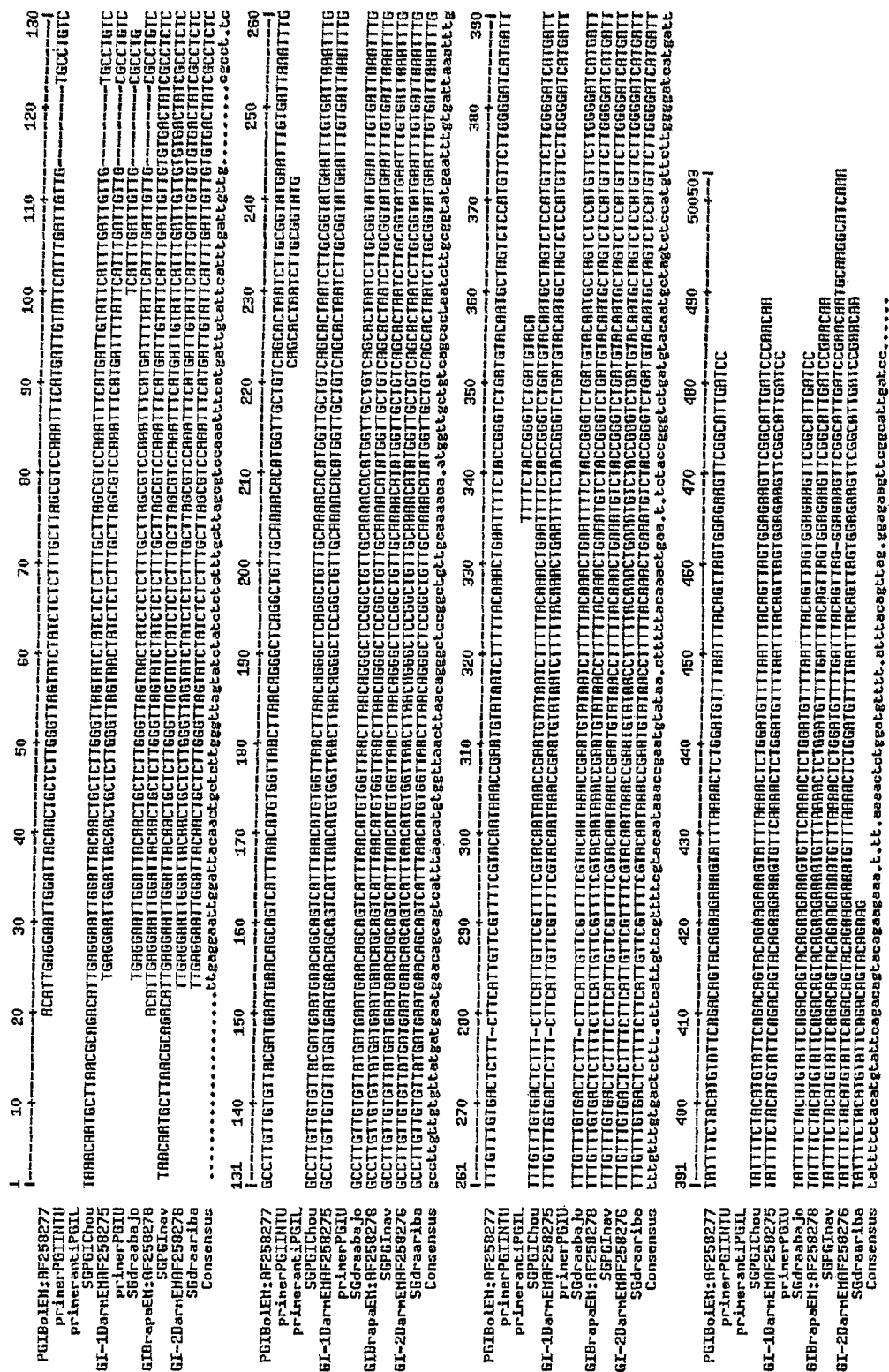

FIG. 4 illustrates PGIol primer localization on the segment of PGI sequence from Data Base.

In that figure:
PGIol: —primer PGIol U (named in SGAP: BnPGIch 1 U)
primer PGIol L (named in SGAP: Bn PGIch 1 L)
PGIint: —primer PGIint U
primer PGIint L (is out side the sequence).

Figure 5:
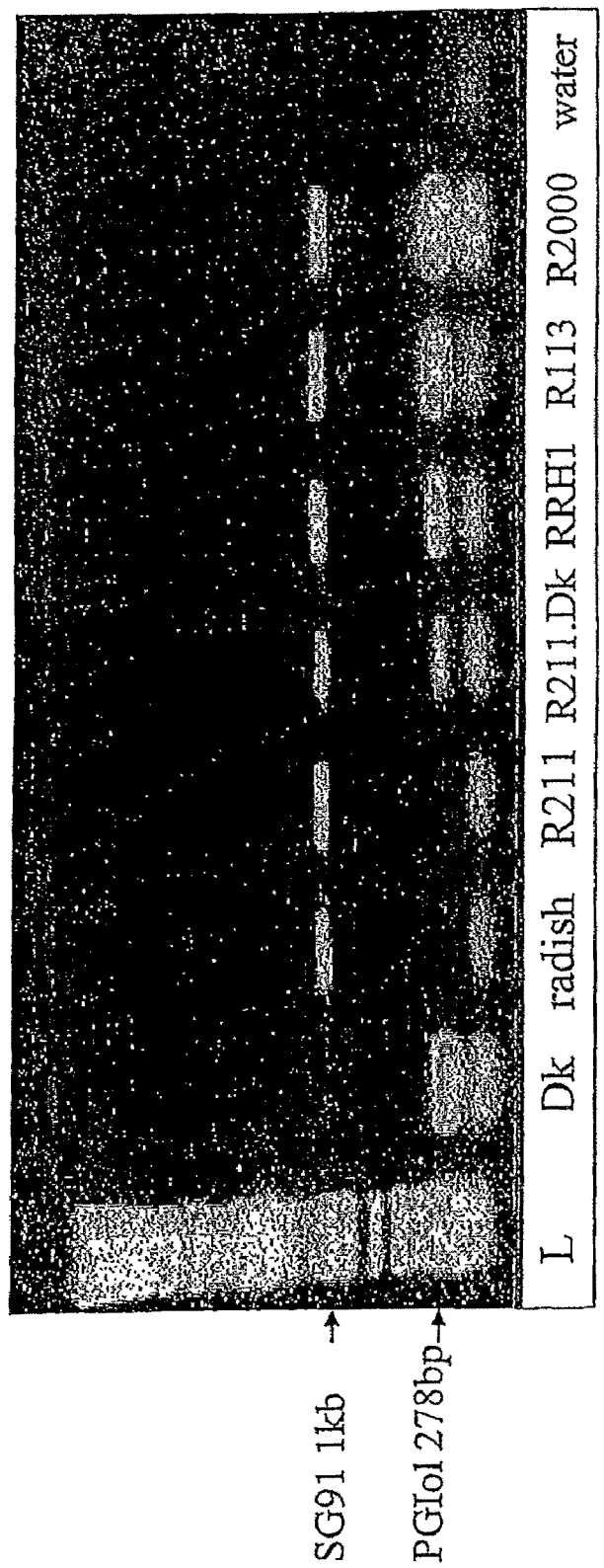

FIG. 5 illustrates electrophoresis gel of PGI-2 gene (PGIol), PCR marker and SG34, a PCR marker close to Rfo.

Figure 6:
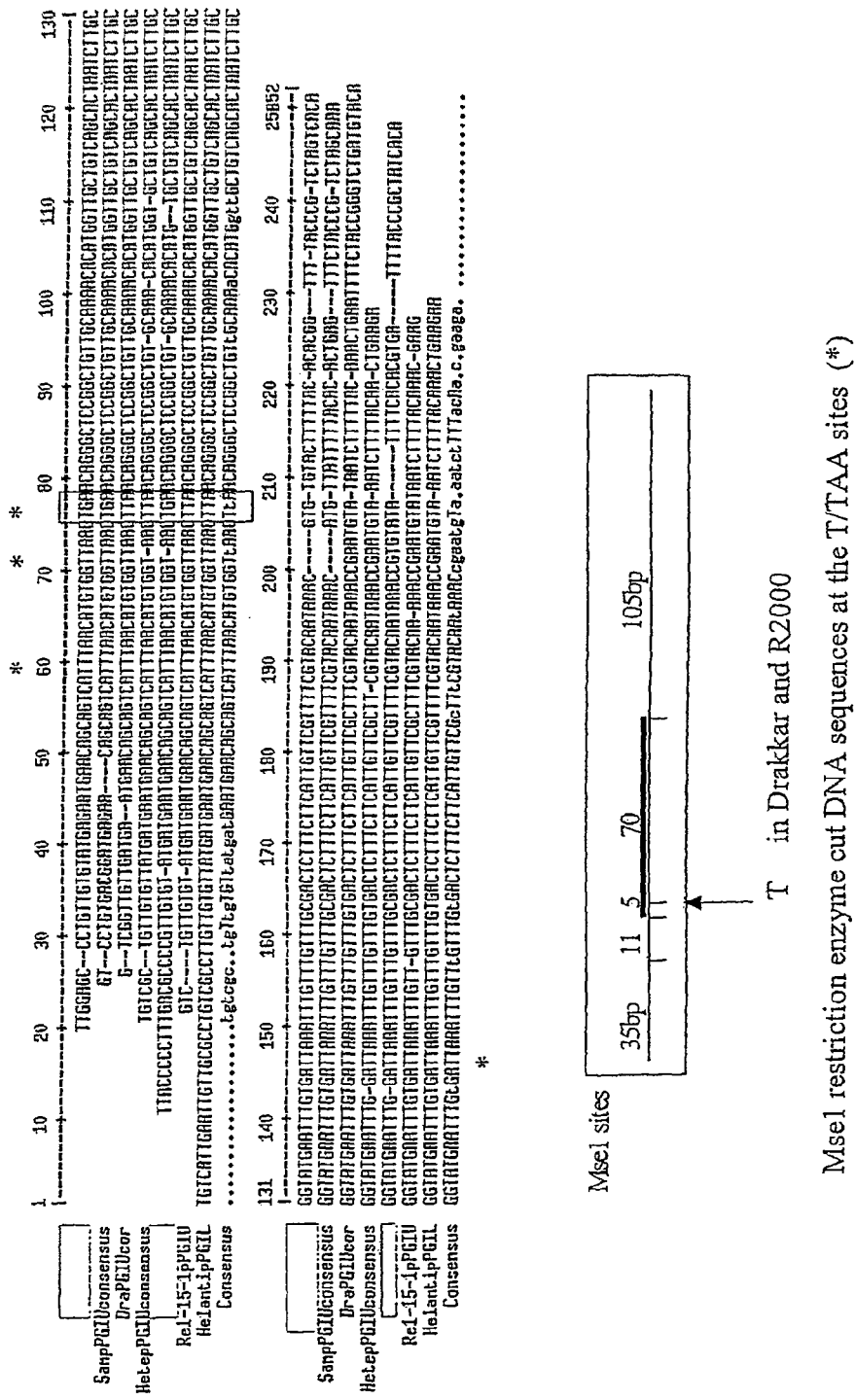

FIG. 6 illustrates Pgi-2 segment of DNA amplified by PCR with PGIol primers.

Figure 7:
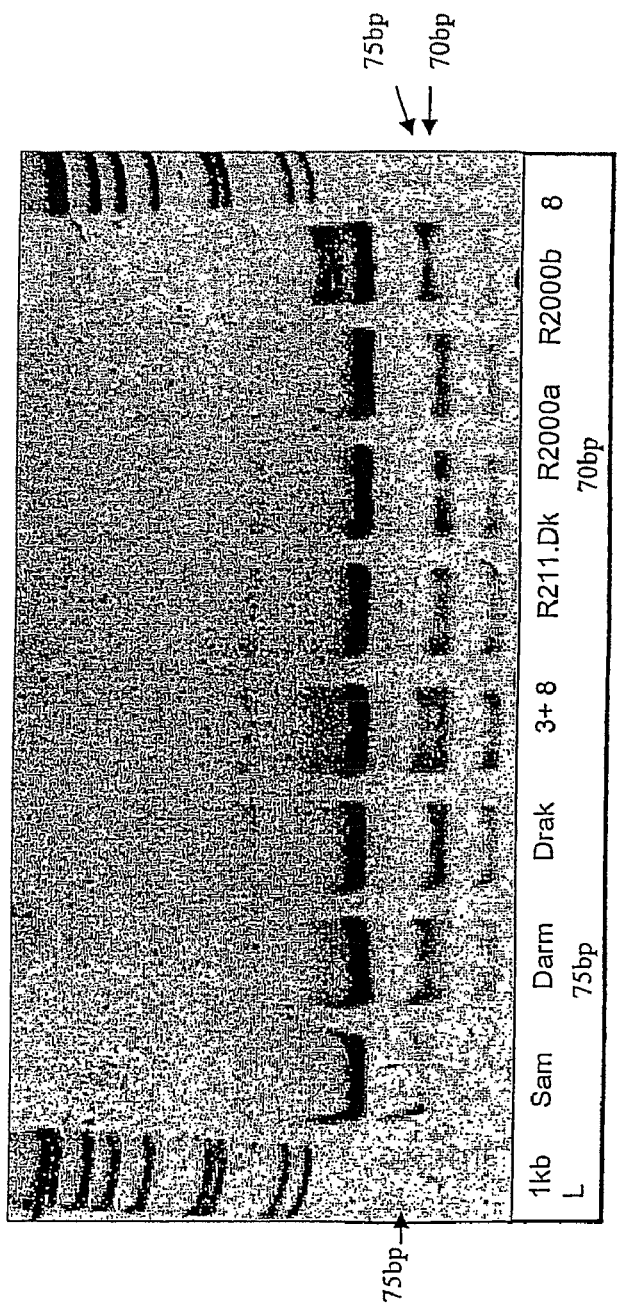

FIG. 7 illustrates digestion of the PCR product PGIol by Msel.

In that figure:
Sam and Darm has a 75 bp band.
Drak, R211.Dk and R2000 showed a 70pb one (Acrylamide 15%).
8 was similar to Samourai (75 bp); mix with Drakkar (70pb) it allowed the visualization of the two bands.

Figure 8:
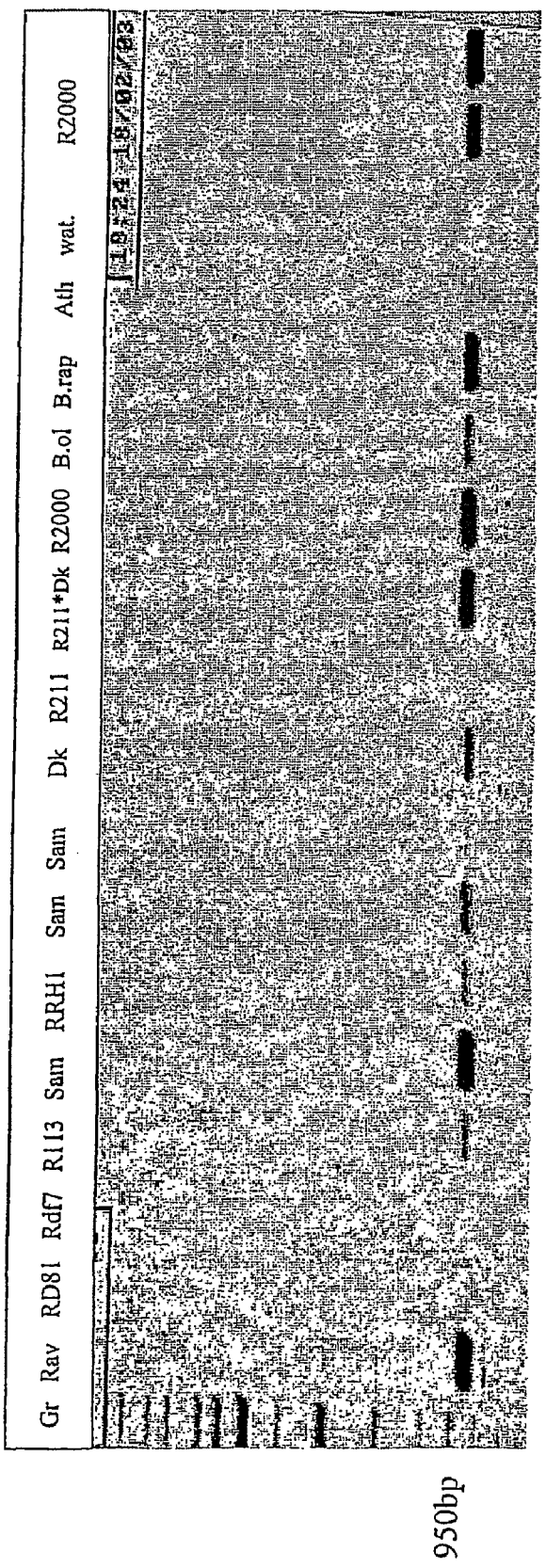

FIG. 8 illustrates electrophoresis agarose gel of PGIUNT marker.

In that figure:
PGIUNT band (about 980 bp) is present in *B.oleracea*, *B.rapa* cv Asko, maintainer and restored lines except in 'R211'.
There is no amplification in radish and *Arabidopsis*.
In various *Brassica* genotypes only one band was amplified. Size band are similar but sequences are different.

Figure 9:
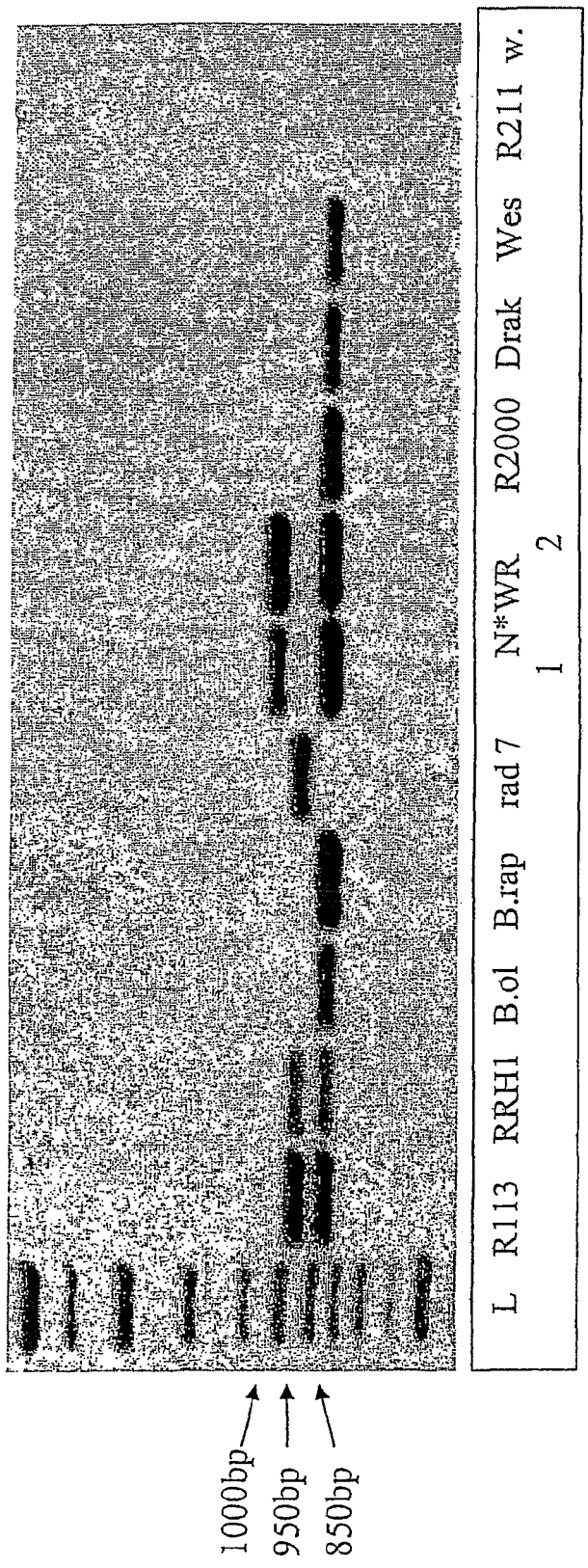

FIG. 9 illustrates electrophoresis gel of PGIint PCR marker.

In that figure PGIint of radish line 7 is of about 950 bp. This band is the same as in the restored RRH1 and R113. It is not found in R211. It is not either in R2000. However the PGIint band is of a similar size of about 870 bp in the various *Brassica* species, but sequences are different.

Figure 10:
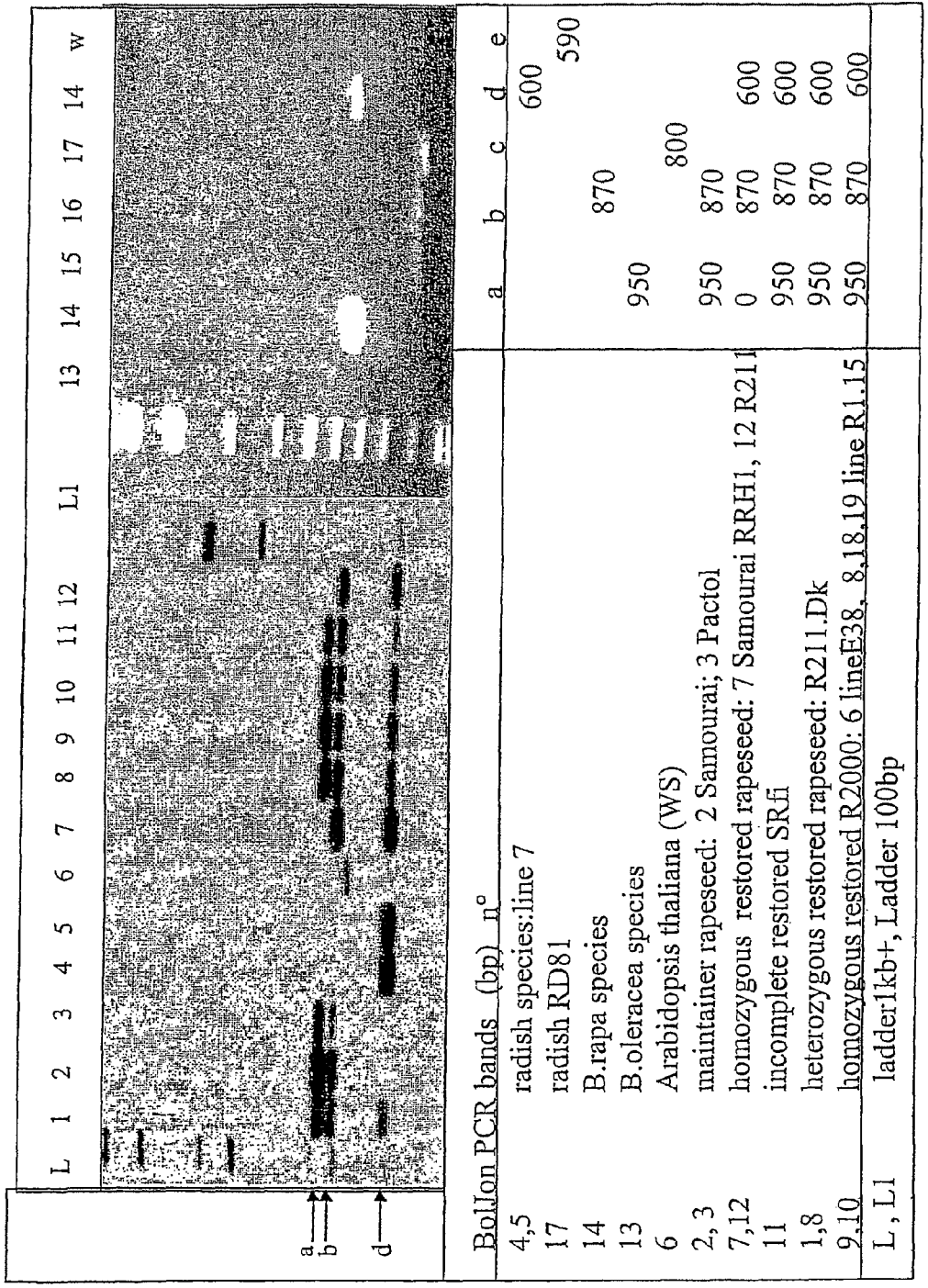

FIG. 10 illustrates electrophoresis agarose gel of BolJon PCR marker.

Figure 11:
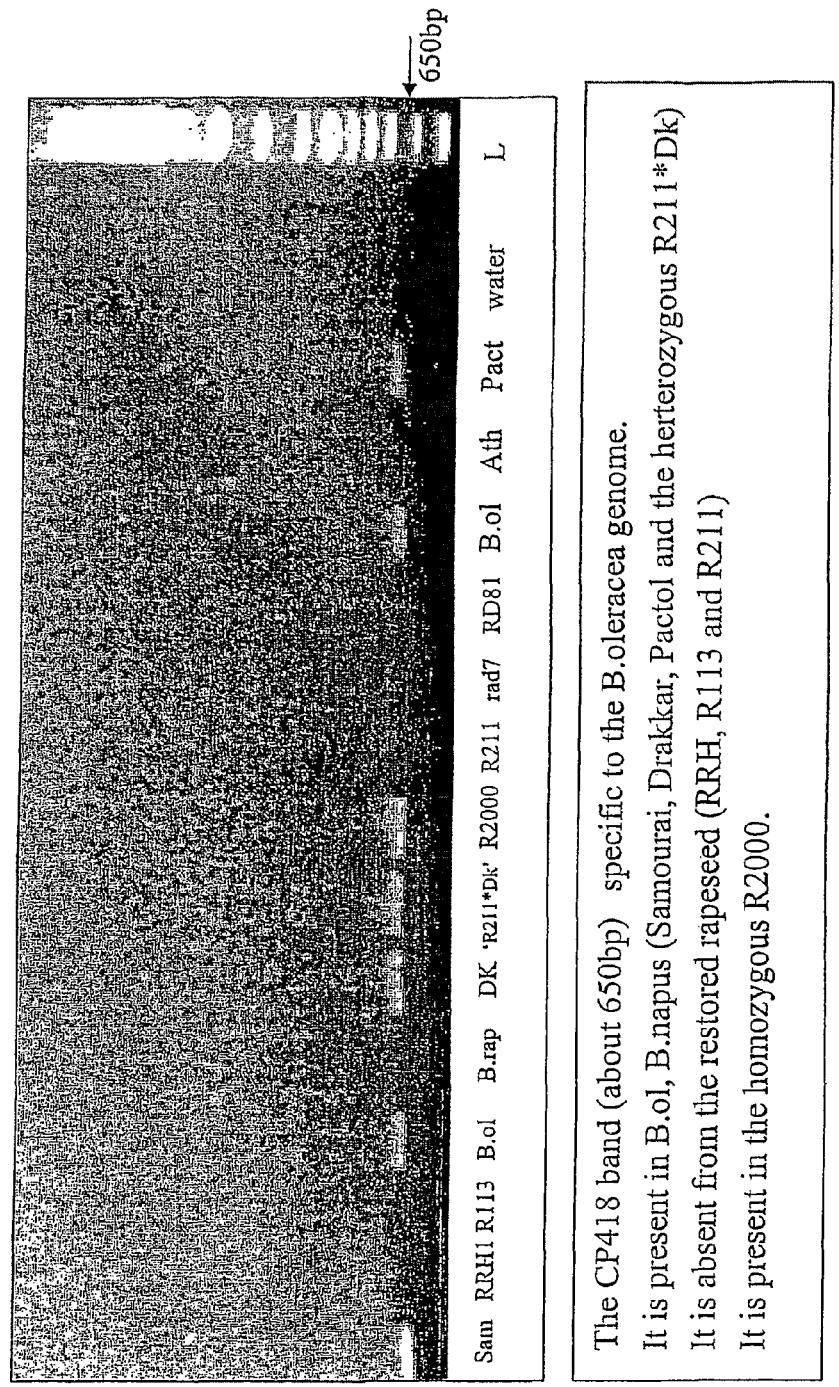

FIG. 11 illustrates electrophoresis agarose gel of CP418 marker.

In that figure, the CP418 band (of about 670 bp) is specific to the *B.oleracea* genome. It is present in *B.ol, B.napus* (Samourai, Drakkar, Pactol and the heterozygous R2111*Dk). It is absent from the restored rapeseed (RRH, R113 and R211). It is present in the homozygous R2000.

FIG. 12 illustrates summary markers table.

FIG. 13 (13(a), 13(b)) illustrates PGIol marker sequence alignment between *Arabidopsis*, Radish, *B.rapa, B.oleracea* and R2000.

FIG. 14 (14(a), 14(b), 14(c), 14(d)) illustrates the PGIint-UNT marker sequence alignment between *Arabidopsis*, Radish, *B.rapa, B.oleracea* and R2000.

FIG. 15 (15(a), 15(b), 15(c)) illustrates the CP418L marker sequence alignment between *Arabidopsis*, Radish, *B.rapa, B.oleracea* and R2000.

Figure 16:
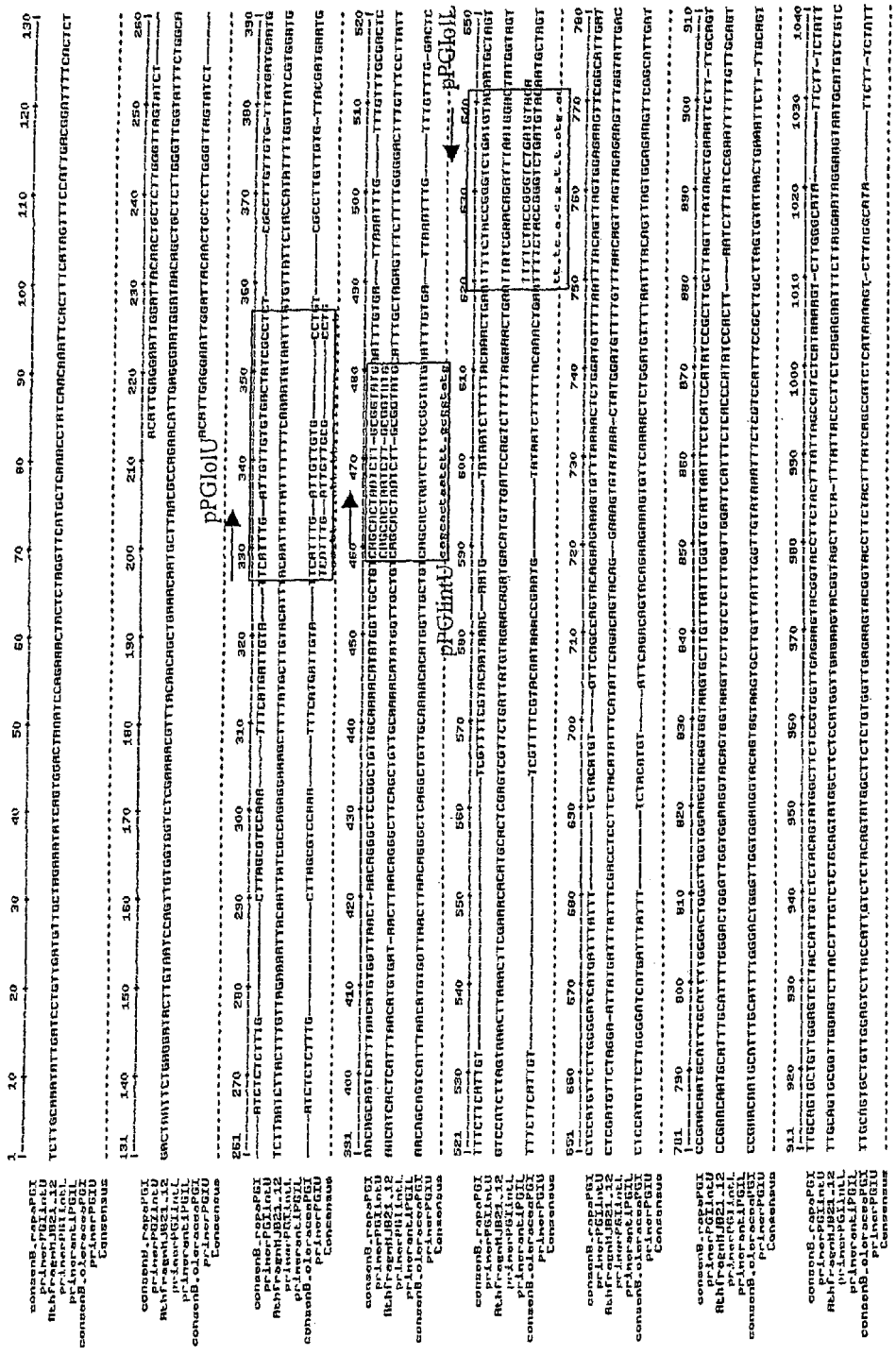

FIG. 16 (16 and 16*bis*) illustrates *Arabidopsis*, Radish and *B.rapa* BolJon markers. There are aligned with DB sequences of *Arabidopsis* (AC007190end-AC011000beginning), the *B.oleracea* EMBH959102 end and EMBH448336 beginning and representative consensus sequences of the SG129markers band 1 and 2 in *B.napus* (in Drakkar and Samourai respectively).

From the point 836 bp, AC07190-AC11000 and GCPATp-BOJ sequences are no longer closely homologous to the *Brassica* sequences.

The radish and *B.rapa* (GCPconsen RsRf BOJ and BR) sequences are still closely homologous to the *B.napus* one, from 858 bp point to the 900 bp and 981 points respectively.

In radish, only partial homology is found on the *Brassica* sequence further down.

In *B.rapa* species cv Asko, the left of its BolJon sequence can be aligned again, after a 78 bp deletion, with those of *B.oleracea* and *B.rapa* in *B. napus* from the 1057 bp point to the BolJon L primer.

Figure 17:
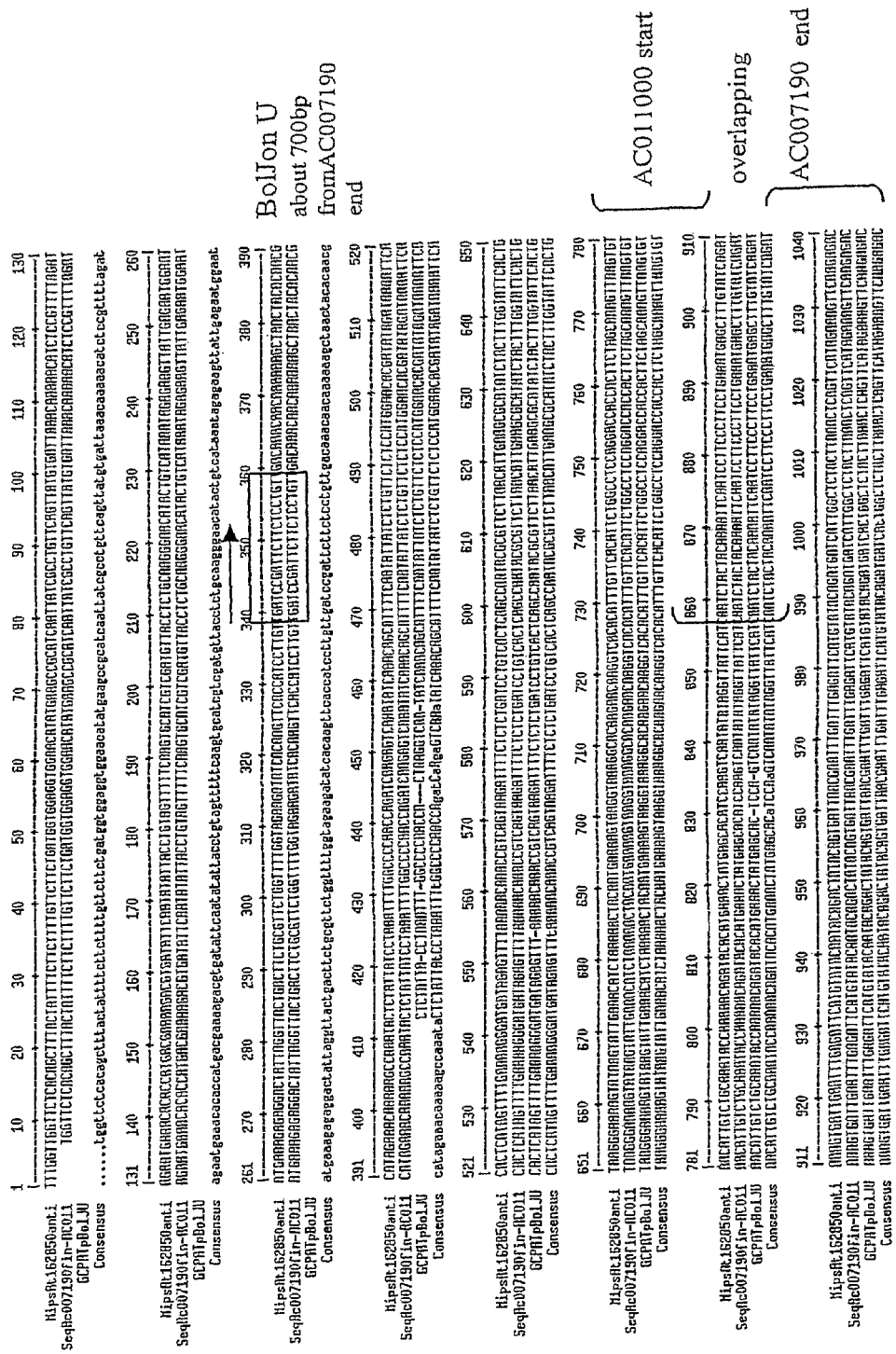

FIG. 17 (17 and 17*bis*) illustrates the localization of Pgi-2 primers on the *Arabidopsis* th MJB21.12 sequence.

DETAILED DESCRIPTION OF THE INVENTION

It should be understood, however, that the examples are given solely by way of illustration of the object of the invention, of which they in no way constitute a limitation.

EXAMPLE I

Method of producing a double low restorer line of *Brassica napus* for Ogura cms presenting a radish introgression, carrying the Rfo restorer gene deleted of the radish Pgi-2 allele and recombined with the Pgi-2 gene from *Brassica oleracea*, and having a good agronomic value characterized by female fertility, a good transmission rate of Rfo and a high vegetative vigor.

Materials And Methods:

Genotypes: The 'R211' line with a deleted radish insertion was crossed to the spring low glucosinolates (GLS) rapeseed 'Drakkar' to produce a F1 progeny ('R211*Dk'). The spring low GLS cms line 'Wesroona' (australian origin) was used for following crosses. The following lines were used as controls in molecular analyses: Winter restored lines derived from 'Samourai' carrying the complete ('RRH1') or incomplete ('R113') introgression as well as European radish line7, Asiatic restored radish D81, hybrid Brasica napus, wild radish, *Brassica oleracea*, and *B.rapa* cv Asko, *Arabidopsis thaliana*.

Gamma ray irradiation: Whole flowering plants were treated with gamma rays from a Co60 source in a controlled area. Sublethal dose of 65 Gray was applied before meiosis.

Testcrosses and F2 production: Irradiated plants were transferred in an insectproof greenhouse after removing flower buds larger than 2 mm. The irradiated F1 progeny was used to handpollinate the cms 'Wesroona' line. The restored derived F1' plants were allowed to produce F2 families harvested individually and precisely sown in a field assay along with non irradiated controls (FIG. 1).

Phenotypic selection: Three visual criteria were scored (on a 1 to 5 scale) over 2 years in field assays, on 1200 F2 offsprings plus 44 controls (82 330 plants):
1-Vegetative vigor,
2-Normality of the ratio of fertile /sterile plants in the F2 segregation, and
3-Female fertility (pod development and seed set).

Advanced selfed generations of the selected families were obtained either in field or greenhouse and produced homozygous lines (F4) for further analysis.

Isozyme analysis was performed as in Delourme R. and Eber F. 1992. *Theor Appl Genet* 85: 222-228, marker development from Fourmann M et al 2002. *Theor Appl. Genet.* 105:1196-1206. PCR products are validated by sequencing. Alignments were made using Blast Ncbi and Uk Crop Net Brassica DB and the Multialin software INRA Toulouse.

Method:

We choose one low GLS spring homozygous restorer line, 'R211', already exhibiting deletions in the introgression (Delourme R. and Eber F. 1992. *Theor Appl Genet* 85: 222-228. Delourme R et al 1998. *Theor Appl Genet* 97: 129-134. Delourme R. et al 1999. 10$^{th}$ *Int. Rapeseed Congress, Canberra*.). Several molecular markers are missing on either side of Rfo, such as spATCHIA (Fourmann M et al 2002. *Theor Appl. Genet.* 105:1196-1206), spSG91 (Giancola S et al 2003 *Theor Appl. Genet.* (in press)). 'R211' lost the isozyme expression of the Pgi-2 allele of the radish gene but also the one of Pgi-2 allele of *B.oleracea* genome (1,2). Moreover, the homozygous 'R211' shows linked negative traits such as low vigor and very poor seed set. We hypothesized that these plants lack a rapeseed chromosomal segment. The fertile ratio in F2 progenies derived from this material is lower than expected (64% instead of 75%). We initiated the program from this 'R211' line and tried to force recombination between the Rfo carrying introgression from this deleted line and the rapeseed homologous chromosome from a double low *B. napus* line.

Ionizing irradiation is known to induce chromosomal rearrangements by double strand breaks followed by aberrant rejoining of the ends. Gamma-ray irradiation was used on a heterozygous F1 derived from the 'R211' line to induce chromosome breaks, just before meiosis, aiming at a recombination of the deleted radish introgression in the rapeseed genome.

Results:

Very few families were at the best score for the three criteria out of 1200 F2 families tested.

Only one, 'R2000', proved to produce a normal ratio of fertile plants per selfed progeny with a stable recovery of good agronomic traits such as a good female fertility, with a normal seed set compared to 'R211' (FIGS. 2 and 3). This family was obtained from a 6 nm irradiation treatment at a dose flow of 65 Gray per hour. Glucosinolate analysis confirmed its low content.

In FIG. 2 (Seed set on 'R211' and 'R2000') R2000 showed normal inflorescences, with a normal looking architecture.

In FIG. 3 (Number of seeds per pod), we observe:
on the best 'R2000' F4 families in self pollination (Selfings) and in testcrosses
on 'Pactol' cms line on rapeseed and 'R211' controls.

EXAMPLE II

Selection of Markers in the Pgi-2 Gene

PGI isoenzyme analysis: 'R2000' progeny expressed the rapeseed Pgi-2 allele from *B. oleracea* genome, originally lost in 'R211'.

Three PCR markers were defined to characterize the R2000 family compared to the known restorer rapeseed RRH1 and R113.

1) PGIol marker was developed from the BrassicaDB sequences to be specific to the *Brassica* genome. There is no amplification in radish nor in *Arabidopsis* th., but only in *Brassica*, with one 248 by band.

2) PGIint marker amplified a longer part of the Pgi-2 gene, allowing clear distinction between the various tested species *Brassica, Raphanus and Arabidopsis*. The species *B.rapa* and *B.oleracea* were not distinguished by the band size on agarose gel, but by their PGINT band sequence.

3) PGIUnt marker, a combination of the PGI of U and PGI int L primers. This marker had the specificity of the PGIol marker but amplifying a longer part such as PGIint.

II.1 PGIol marker

With the PGIol primers, the 'R211' parental line showed no amplification, while the spring tested lines showed a 248 bp band. Its DNA sequence is homologous to the PGI-2 sequences from the Crop Net UK DB in *Brassica* species and from previous work in our group (named SGAP sequences) (Localization of the primers SG PGI chou, FIG. 4).

It was ortholog of the clone MJB21-12, on the chromosome V, (34543 bp) in *Arabidopsis* (NCBI DB).

PGIol plus SG34 to set an Homozygocity test:

The combined use of two sets of primers in a mix PCR, PGIol marking the Pgi-2 gene absent in the homozygote restored plant and SG34 (from S. Giancola et al, Giancola S et al 2003 *Theor Appl. Genet.* (in press)), a very close marker to the Rfo gene, was set up to discriminate homozygous from heterozygous plant among the fertile plants segregating in F2 progenies derived from 'R211'. In place of using SG34, it is possible to use any other marker close to or in the Rfo gene.

Only one family R2000 showed no difference between homozygote and heterozygote offsprings:

The Pgi-2 gene is present in the R2000 homozygote, which is not the case for the parental homozygous R211.

In FIG. 5 (PGIol and SG34 PCR markers):

The homozygous 'R2000' family has recovered the PGIol band.

DNA sequence of the band confirmed the homology with the known *Arabidopsis* and *Brassica* Pgi-2 sequence. Control genotypes (Drakkar, Pactol, and, Samourai, Darmor) had the same pattern on the gel. Sequence of this common band allowed to confirm their high homology as they were quasi similar except one base substitution.

The homozygous 'R2000' family has recovered the PGIol band of the *Brassica oleracea* type. It was distinct from the known restorer of the Samourai group.

This amplified part of the Pgi-2 is very conserved and hardly any differences were shown among the various genotypes. A longer part of Pgi-2 gene was investigated.

II.2 PGIUNT and PGIint markers

Electrophoresis Patterns of PCR products:

PGIUNT marker: A second reverse primer, PGIint L, was designed further down the Pgi-2 sequence, to amplify as well conserved and as variable regions of the gene. When used with the PGIol U primer, it amplifies a 980 bp band only in *Brassica* genomes.

R211 didn't show any band, The homozygous 'R2000' showed the PGIUNT band as in the Drakkar parent.

In FIG. 8 (PGIUNT marker):

PGIint marker amplified a segment of PGIUNT. The upper primer PGIint allows the amplification in all tested species, allowing a clear distinction between *Arabidopsis*, Radish and *Brassica*. *B.rapa* and *B.oleracea* were not distinguished by the band size on agarose gel, but by their PGIint sequence. All tested restored genotypes, but the 'R211' line, exhibited the European radish band and one *Brassica* band, homologous to the *B.rapa* one.

The homozygous 'R2000' didn't show the radish PGIint band, as in the deleted 'R211' parental line, but showed one *Brassica* band, homologous to the *B. oleracea* one.

Electrophoresis of PGIint marker is represented in FIG. 9.

Sequence analysis:

Comparison of the PGI sequences from the data bases. A PGI segment of about 490 bp is known.

Sequences of a segment of about 490 bp from different genotypes (*B. oleracea, B. rapa, B. napus*) have been studied in our laboratory group and some sequences were given to Brassica Crop Net DB: EMAF25875 to 25788 by M.Fouramnn (4) These sequences are very conserved.

Comparison of the *B. rapa* et *B.oleracea* species PGI sequences (FIGS. 13 and 14):

Comparison between PGI sequences we have obtained from the tested genotypes of *B.oleracea* and *B.rapa* species, showed that they were distinct by 21 base substitutions. Theses substitutions allowed to distinguish PGIint sequences from the other tested genotypes of rapeseed, homologous to either *B.rapa* cv Asko (RRH1 and R113) or *B.oleracea* (Drakkar, R211*DK but also R2000).

EXAMPLE III

Selection of Marker in a Region Close to Rfo

Markers surrounding the Rfo gene in the radish insertion were determined in order to facilitate the Rfo gene cloning (Desloires S et al 2003 *EMBO reports* 4, 6:588-594). One of these, the SG129 PCR marker was located very close to Rfo (Giancola S et al 2003 *Theor Appl. Genet.* (in press)): it co-amplified distinct bands in *B.oleracea* and *B.rapa* genomes of *B.napus*, but the radish band was very difficult to see on an agarose gel.

The target SG129 sequence was ortholog of a clone (AC011000, at the locus F16P17) in *Arabidopsis thaliana*. This clone overlapped an *Arabidopsis* adjacent contig clone (AC07190).

From the Brassica Crop Net DB, we found one *B.oleracea* clone, (EMBE448336, 764 bp) blasting with the beginning of the A011000, and a second *B.oleracea* clone (EMBE53971), distant from about 300 bp on the *Arabidopsis* map, that blasted with the end of AC07190.

We designed a new PCR marker, BolJon, between the two *B.oleracea* clones. We verified that it allowed amplification of a specific PCR bands in the different genotypes compared here.

In FIG. 16 (electrophoresis gel of BolJon PCR products):
In *Arabidopsis*, a BolJon 815 bp band was amplified, homologue to the overlapping segment of the contigs.
In Brassiceae diploid species, BolJon marker showed distinct bands: one of 950 bp in *B.oleracea* and one of 870 bp in *B.rapa*. It showed that the two *B.oleracea* clones (EMBE53971 and EMBE448336) are in sequence continuity in *Brassica* genome as it is for the ortholog sequences in *Arabidopsis*.
In *B.napus*, these two bands are co-amplified in the maintainer lines, Samourai or Drakkar.
In radish line7, one BolJon band was amplified of about 630 by long. The band of the restored radish cmsRd81 was slightly smaller.
In all the restored rapeseed lines, one of the BolJon bands was of the same size as the radish line7. BolJon is a marker of the radish introgression.
The homozygous restored rapeseed lines, 'RH1', 'R113' and also 'R211', only showed the *B.rapa* band and the 630 bp radish band by suggesting the *B.oleracea* ortholog of the target gene is absent or has been modified when the radish segment of chromosome was inserted into the rapeseed *B.oleracea* constitutive genome.

'R2000' homozygote plants showed radish PCR BolJon, plus the two *Brassica* BolJon bands, again having recovered the *B.oleracea* one, lost in 'R211' and other restorer lines.

We designed a primer, pCP418L, specific of the *B.oleracea* genome in the tested species. With the SG129 U primer it amplified only one PCR band (670 bp) in the *B.oleracea* species. (FIG. 17)

There was no amplification in *B.rapa*, in radish, nor in *Arabidopsis*, but there was a clear CP418 band in *B. napus* maintainer lines. Its sequence was strictly homologous to the EMBE448336 sequence. This marker was in a very conserved DNA sequence allowing no polymorphism between genotypes except by presence/absence.

In RRH1, R113 and in R211 there was no CP418 band, indicating as previously that the *B.oleracea* ortholog of the target gene is absent or has been modified following the radish insertion.

'R2000' homozygote plants showed CP418 band, again having recovered the specific *B.oleracea* one.

In the present invention, a new recombined low GLS restorer line has been selected with a good female fertility. The poor value of line 'R211' allowed selection in the field for a rare recombination event and characterization the 'R2000' family.

The homozygous 'R2000' presents a unique combination of the PGIol, PGIUNT, PGIint and BolJon markers when compared with the rapeseed restorer analyzed yet:

PGIinT marker showed that the homozygous restored rapeseed lines, RRH1 and R113 presented the European radish band plus one *Brassica* band, homologous to *B.rapa* genome. 'R2000' shows no radish band, lost as in its parental deleted line R211, but showed one *Brassica* band homologous to *B.oleracea*. The ortholog PGIint sequence in its *B.rapa* genome is not amplified with this marker in R211 and Drakkar genetic background.

PGIol marker and PGIUNT marker sequences in restored lines RRH1 and R113 were homologous to the *B.rapa* cv Asko one. In 'R2000', PGIUNT sequence is homologous to *B.oleracea*. The ortholog PGIUnt sequence in its *B.rapa* genome is not amplified with this marker in R211 and Drakkar genetic background. BolJon marker showed that the homozygous restored rapeseed lines, including 'R211' presented the European radish band plus only the *B.rapa* one. 'R2000' shows the two bands of 'R211' plus the recovered *B.oleracea* BolJon band.

CP418 marker showed that 'R2000' recovered this conserved *B.oleracea* segment.

Our hypothesis is that a recombination event took place in the pollen mother cell which gave rise to 'R2000' plants. The deleted radish introgression was then integrated to the normal homologous chromosome segment, carrying the *B.oleracea* type Pgi-2 gene and BolJon target sequence, characterized by these markers, probably from the Drakkar '00' genome present in the irradiated heterozygous 'R211*DK'.

The pattern observed for BolJon suggests that the recombination event resulted in a particular duplicated region, one from radish and one *B.oleracea*, in the 'R2000' family.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. Double low restorer line of *Brassica napus* for Ogura cytoplasmic male sterility (cms) presenting a Rfo insertion deleted of the radish Pgi-2 allele and recombined with the Pgi-2 gene from *Brassica oleracea*, and having an agronomic value characterized by female fertility, a transmission rate of Rfo and a vegetative vigour, characterized in that said double low restorer line of *Brassica napus* for Ogura cms presents the five markers PGIol, PGIUNT, PGIint, BolJon and CP418, wherein said markers comprise the following sequences:
   PGIol marker: SEQ ID NO:1;
   PGIUNT marker: SEQ ID NO:2;
   PGIint marker: SEQ ID NO:3;
   BolJon marker: SEQ ID NO:4; and
   CP418 marker: SEQ ID NO:5.

2. Double low restorer line of *Brassica napus* according to claim 1, wherein the BOlJon marker exhibits a radish band, a *Brassica oleracea* band and a *Brassica rapa* band in a homozygote of said restorer line.

3. Seeds of *Brassica* plant developed from the *Brassica* line of claim 1 wherein the said seeds comprise the Rfo insertion deleted of the radish Pgi-2 allele and recombined with the Pgi-2 gene from *Brassica oleracea*.

4. A method for characterizing recombed restorer lines of *Brassica napus* for Ogura cms presenting a Rfo insertion deleted of the radish Pgi-2 allele and recombined with the Pgi-2 gene from *Brassica oleracea*, and having an agronomic value characterized by female fertility, transmission rate of Rfo and vegetative vigour; comprising a step wherein the presence of the five markers PGIol, PGIUNT, PGIint, BolJon and CP418 is detected in said recombined restorer lines and wherein said markers comprise the following sequences:
   PGIol marker: SEQ ID NO:1;
   PGIUNT marker: SEQ ID NO:2;
   PGIint marker:SEQ ID NO:3; and
   BolJon marker:SEQ ID NO:4,
      wherein the marker PGIol is amplified using primers PGIol U, comprising SEQ ID NO:6 and PGIol L, comprising SEQ ID NO:7;
      the marker PGIint is amplified using primers PGIint U, comprising SEQ ID NO:8 and PGIint L, comprising SEQ ID NO:9;

the marker BolJon is amplified using primers BolJon U, comprising SEQ ID NO:12 and BolJon L, comprising SEQ ID NO:13; and the marker PGIUNT is amplified using primers PGIol U comprising SEQ ID NO:6 and PGIint L, comprising SEQ ID NO:9.

5. A method of producing double low restorer lines of *Brassica napus* for Ogura cytoplasmic male sterility (cms) presenting a radish insertion carrying the Rfo restorer gene deleted of the radish Pgi-2 allele and recombined with the Pgi-2 gene from *Brassica oleracea*, and having an agronomic value characterized by female fertility, transmission rate of Rfo and vegetative vigour, comprising:

a) crossing double low cms lines of spring *Brassica napus* comprising the deleted radish insertion comprising the Rfo restorer gene, with the double low line of spring Drakkar for forming heterozygous restored plants of *Brassica napus*;

b) irradiating before meiosis the heterozygous restored plants obtained in step a) with gamma ray irradiation;

c) crossing pollen from flowers obtained in step b) with the cms double low spring Wesroona line;

d) testing the progeny with the five markers PGIol, PGIUNT, PGIint, BolJon and CP418; and e) selecting the progeny lines presenting the combination of said five markers, and wherein said markers comprise the following sequences:

PGIol marker: SEQ ID NO:1;
PGIUNT marker: SEQ ID NO:2;
PGIint marker:SEQ ID NO:3;
BolJon marker:SEQ ID NO:4; and
CP418 marker: SEQ ID NO:5.

6. The method of claim 5, wherein said irradiation dose in step b) is 65 Gray during 6 mn.

7. Seeds of a *Brassica* plant developed from the *Brassica* line obtained by the method of claim 5 wherein the said seeds comprise the Rfo insertion deleted of the radish Pgi-2 allele and recombined with the Pgi-2 gene from *Brassica oleracea*.

8. Seeds of a *Brassica napus* obtained by the method of claim 5 deposited in NCIMB Limited, 23 St Machar Drive, Aberdeen, Scotland, AB24 3RY, UK on Jul. 4, 2003, under reference number NCIMB41183.

9. A method of producing *Brassica napus* hybrid plants, comprising:

a) providing a restorer line produced by the method of claim 5 and bred to be homozygous;

b) using said restorer line in a hybrid production field as the pollinator;

c) using cms sterile plants in a hybrid production field as the hybrid seed producing plant; and d) harvesting the hybrid seed from the male sterile plant.

10. Seeds of a *Brassica napus* obtained by the method of claim 9 wherein the said seeds comprise the Rfo insertion deleted of the radish Pgi-2 allele and recombined with the Pgi-2 gene from *Brassica oleracea*.

* * * * *

SEQUENCE LISTING

<160> NUMBER OF SEQ ID NOS: 14

<210> SEQ ID NO 1
<211> LENGTH: 248
<212> TYPE: DNA
<213> ORGANISM: Brassica napus
<220> FEATURE:
<223> OTHER INFORMATION: PGIo1 marker

<400> SEQUENCE: 1

```
tcatttgatt gttgcgcctg tcgccttgtt gtgttatgat gaatgaacag cagtcattta    60
acatgtggtt aacttaacag ggctccggct gttgcaaaac acatggttgc tgtcagcact   120
aatcttgcgg tatgaatttg tgattaaatt tgtttgtttg tgactctttc ttcattgttc   180
gttttcgtac aataaaccga atgtataatc tttttacaaa ctgaattttc taccgggtct   240
gatgtaca                                                            248
```

<210> SEQ ID NO 2
<211> LENGTH: 979
<212> TYPE: DNA
<213> ORGANISM: Brassica napus
<220> FEATURE:
<223> OTHER INFORMATION: PGI-UNT R2000 marker

<400> SEQUENCE: 2

```
tcatttgatt gttgcgcctg tcgccttgtt gtgttatgat gaatgaacag cagtcattta    60
acatgtggtt aacttaacag ggctccggct gttgcaaaac acatggttgc tgtcagcact   120
aatcttgcgg tatgaatttg tgattaaatt tgtttgtttg tgactctttc ttcattgttc   180
gttttcgtac aataaaccga atgtataatc tttttacaaa ctgaattttc taccgggtctg   240
atgtacaatg ctagtctcca tgttcttggg gatcatgatt tattttctac atgtattcag   300
acagtacaga agaaagtgtt caaaactctg gatgttttaa tttacagtta gtggagaagt   360
tcggcattga tccgaacaat gcatttgcat tttgggactg ggttggtgga aggtacagtg   420
gtaagtgctt gtttatttgg ttgtataaat ttctcgtcca tttccgcttg cttagtgtat   480
aactgaaatt cttttgcagt ttgcagtgct gttggagtct taccattgtc tctacagtat   540
ggcttctctg tggttgagaa gtacggtacc ttctacttta tcagccatct cataaaatgt   600
cttaggcata ttctttctat tttatttccc tcttaatgat ttcttctttt ttttattgca   660
ttcccgtttt attttcaaaa gttgttactg tctctaaatc aagaagaaac cttcttagta   720
gatccagctg atattcagcc ttttttaaat tggactgcag gttttttaaag gggagcttca   780
agcattgata agcatttcca gtccacaccg tttgagaaga atatacccgt gagttgcatt   840
agttgtgtga ttatacagtt ttcttgtctt tttgctatgt ccatcaacac tagagattcg   900
tgaagttatt agtgtagtca acgcataggg agaggtgatt ggtgactttt ggacgatttc   960
aggtgcttta gggttattg                                                979
```

<210> SEQ ID NO 3
<211> LENGTH: 866
<212> TYPE: DNA
<213> ORGANISM: Brassica napus
<220> FEATURE:
<223> OTHER INFORMATION: PGI-int R2000 marker

<400> SEQUENCE: 3

```
cagcactaat cttgcggtat gaatttgtga ttaaatttgt tgtttgtga ctctttcttc    60
```

-continued

| | |
|---|---|
| attgttcgtt ttcgtacaat aaaccgaatg tataatcttt tacaaactga attttctacc | 120 |
| gggtctgatg tacaatgcta gtctccatgt tcttggggat catgatttat tttctacatg | 180 |
| tattcagaca gtacagaaga aagtgttcaa aactctggat gttttaattt acagttagtg | 240 |
| gagaagttcg gcattgatcc gaacaatgca tttgcatttt gggactgggt tggtggaagg | 300 |
| tacagtggta agtgcttgtt tatttggttg tataaatttc tcgtccattt ccgcttgctt | 360 |
| agtgtataac tgaaattctt ttgcagtttg cagtgctgtt ggagtcttac cattgtctct | 420 |
| acagtatggc ttctctgtgg ttgagaagta cggtaccttc tactttatca gccatctcat | 480 |
| aaaatgtctt aggcatattc tttctatttt atttccctct taatgatttc ttcttttttt | 540 |
| tattgcattc ccgttttatt ttcaaaagtt gttactgtct ctaaatcaag aagaaacctt | 600 |
| cttagtagat ccagctgata ttcagccttt tttaaattgg actgcaggtt tttaaagggg | 660 |
| agcttcaagc attgataagc atttccagtc cacaccgttt gagaagaata tacccgtgag | 720 |
| ttgcattagt tgtgtgatta tacagttttc ttgtcttttt gctatgtcca tcaacactag | 780 |
| agattcgtga agttattagt gtagtcaacg catagggaga ggtgattggt gacttttgga | 840 |
| cgatttcagg tgctttaggg ttattg | 866 |

<210> SEQ ID NO 4
<211> LENGTH: 957
<212> TYPE: DNA
<213> ORGANISM: Brassica napus
<220> FEATURE:
<223> OTHER INFORMATION: BolJon marker R2000

<400> SEQUENCE: 4

| | |
|---|---|
| gatccgattc ttctcctgtt gagatcagct ccaaacatca acaacttgt acacaaatat | 60 |
| ctttacttgc taaatggaac atgacaagag atagaaaatc ttgctcatag tattgtacaa | 120 |
| gggataacag tgtagaaaac aaaccgtctg taagattttc tccctgatcc tctcacttaa | 180 |
| ccagtaggcg tttttcacat tgaagcgcat atctactttg gtattcactg aataaaaaaa | 240 |
| gaaagctggt aacatgtgaa ggatatacaa gcattgatac accaagtagt cacaaactac | 300 |
| attataaagg tcagacccttt gttcacattc tggcctccag gaccaccgct tctagcaaag | 360 |
| ttaagcgtaa catggtctgc acgtatacaa atgaaaatgt ttctatcaaa atcctataaa | 420 |
| atagagctct ataacattgt cgatacatag tttcactaac tctgcaagta ctaaacacat | 480 |
| atacaaacaa aactatgcga acagatcaaa actactacag aacacagttc tatgacactg | 540 |
| tcgatagtaa catcctctgc aagtaccaaa gagatagcaa atgaaactat gtaaacaaat | 600 |
| caaaattcta aatttctcca tcacaaggac ctacagaata gagttatcat aacattttct | 660 |
| gtaaatattt ccatcaaaat gactagagaa cagagttctt ataacattat ctgtaaatgt | 720 |
| tccaacaaaa ccactacata gcagagttct tataacattg tctgtaaatg tccaatcaaa | 780 |
| accactacag aacaaagctc ctataacatt gtttatacaa agtttcacta aatctacaaa | 840 |
| ctttccccgt aaatgagctt aatatcaccc aaagatgttt caatcagata aagagtacga | 900 |
| catcgttttg agattagaac aaactgaaac ttacgtagag tgatttgagg agtaggc | 957 |

<210> SEQ ID NO 5
<211> LENGTH: 672
<212> TYPE: DNA
<213> ORGANISM: Brassica napus
<220> FEATURE:
<223> OTHER INFORMATION: CP418L marker R2000

<400> SEQUENCE: 5

```
aatttctcca tcacaaggac ctacagaata gagttatcat aacatttct gtaaatattt    60 ccatcaaaat gactagagaa cagagttctt ataacattat ctgtaaatgt tccaacaaaa   120
ccactacata gcagagttct tataacattg tctgtaaatg tccaatcaaa accactacag   180
aacaaagctc ctataacatt gtttatacaa agtttcacta atctacaaa ctttccccgt    240 aaatgagctt aatatcaccc aaagatgttt caatcagata aagagtaacg acatcgtttt   300
gagattagaa caaactgaaa cttacgtaga gtgatttgag gagtaggctc gttgccagca   360
gagctagctc tctcctccgc ctcatgaagc atctgttgca cctgagacaa ccgtgacgaa   420
actttccgat caccgccacc agaattcgac gccgcgcatc ggaaggatcc gaatcggaa    480 ctgagtgaac ccgagcgatc ccgggagtgc gacggagcga tgggaaaaga gagtggcacg   540
atttcgacga agagtggaag aggagagggt ggtggataaa ctcgcgtatg atcaagttcg   600
tcatcgtcct gattgccgcc attttttttg tcagggcgct ctgtggctta aagtttccg    660 atgtcaatga ac                                                     672
```

<210> SEQ ID NO 6
<211> LENGTH: 20
<212> TYPE: DNA
<213> ORGANISM: artificial sequence
<220> FEATURE:
<223> OTHER INFORMATION: PGIo1 U primer

<400> SEQUENCE: 6
tcatttgatt gttgcgcctg                                              20

<210> SEQ ID NO 7
<211> LENGTH: 23
<212> TYPE: DNA
<213> ORGANISM: artificial sequence
<220> FEATURE:
<223> OTHER INFORMATION: PGIo1 L primer

<400> SEQUENCE: 7
tgtacatcag acccggtaga aaa                                          23

<210> SEQ ID NO 8
<211> LENGTH: 21
<212> TYPE: DNA
<213> ORGANISM: artificial sequence
<220> FEATURE:
<223> OTHER INFORMATION: PGIint U primer

<400> SEQUENCE: 8
cagcactaat cttgcggtat g                                            21

<210> SEQ ID NO 9
<211> LENGTH: 21
<212> TYPE: DNA
<213> ORGANISM: artificial sequence
<220> FEATURE:
<223> OTHER INFORMATION: PGIint L primer

<400> SEQUENCE: 9
caataaccct aaaagcacct g                                            21

<210> SEQ ID NO 10
<211> LENGTH: 20
<212> TYPE: DNA
<213> ORGANISM: artificial sequence
<220> FEATURE:
<223> OTHER INFORMATION: PGIo1 U primer -continued

```
<400> SEQUENCE: 10
tcatttgatt gttgcgcctg                                          20

<210> SEQ ID NO 11
<211> LENGTH: 21
<212> TYPE: DNA
<213> ORGANISM: artificial sequence
<220> FEATURE:
<223> OTHER INFORMATION: PGIint L primer

<400> SEQUENCE: 11
caataaccct aaaagcacct g                                        21

<210> SEQ ID NO 12
<211> LENGTH: 21
<212> TYPE: DNA
<213> ORGANISM: artificial sequence
<220> FEATURE:
<223> OTHER INFORMATION: BolJon U primer

<400> SEQUENCE: 12
gatccgattc ttctcctgtt g                                        21

<210> SEQ ID NO 13
<211> LENGTH: 21
<212> TYPE: DNA
<213> ORGANISM: artificial sequence
<220> FEATURE:
<223> OTHER INFORMATION: BolJon L primer

<400> SEQUENCE: 13
gcctactcct caaatcactc t                                        21

<210> SEQ ID NO 14
<211> LENGTH: 21
<212> TYPE: DNA
<213> ORGANISM: artificial sequence
<220> FEATURE:
<223> OTHER INFORMATION: pCP418 L primer

<400> SEQUENCE: 14
aatttctcca tcacaaggac c                                        21
```